US009173558B2

(12) United States Patent
Huth et al.

(10) Patent No.: US 9,173,558 B2
(45) Date of Patent: Nov. 3, 2015

(54) METHOD FOR CALCULATING TEAR FILM LIPID AND AQUEOUS LAYER THICKNESSES AND CORNEAL SURFACE REFRACTIVE INDEX FROM INTERFEROMETRY DATA

(71) Applicant: Abbott Medical Optics Inc., Santa Ana, CA (US)

(72) Inventors: Stanley Huth, Newport Beach, CA (US); Denise Tran, Irvine, CA (US); Huawei Zhao, Irvine, CA (US); Alkan Gulses, Los Angeles, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 121 days.

(21) Appl. No.: 14/058,564

(22) Filed: Oct. 21, 2013

(65) Prior Publication Data

US 2014/0118699 A1    May 1, 2014

Related U.S. Application Data

(63) Continuation of application No. 13/310,026, filed on Dec. 2, 2011, now Pat. No. 8,602,557.

(51) Int. Cl.
*A61B 3/10* (2006.01)
*A61B 3/103* (2006.01)
*A61B 3/15* (2006.01)
*A61F 9/008* (2006.01)

(52) U.S. Cl.
CPC ............... *A61B 3/1015* (2013.01); *A61B 3/101* (2013.01); *A61B 3/103* (2013.01); *A61B 3/152* (2013.01); *A61F 2009/00872* (2013.01)

(58) Field of Classification Search
CPC . A61F 9/00804; A61F 9/00814; A61F 9/008; A61F 2009/00872; A61F 2009/0088; A61B 3/152

USPC ............... 351/206, 208–209, 220, 246; 606/5
See application file for complete search history.

(56) References Cited

U.S. PATENT DOCUMENTS

| 6,236,459 | B1 | 5/2001 | Negahdaripour et al. |
| 7,281,801 | B2 | 10/2007 | Wang |
| 7,758,190 | B2 | 7/2010 | Korb et al. |
| 7,866,819 | B2 | 1/2011 | Tuan |
| 7,963,655 | B2 | 6/2011 | Huth et al. |
| 2004/0212781 | A1 | 10/2004 | Mihashi et al. |
| 2006/0109423 | A1 | 5/2006 | Wang |
| 2008/0273171 | A1 | 11/2008 | Huth et al. |
| 2009/0201465 | A1* | 8/2009 | Huth .............................. 351/205 |
| 2010/0253907 | A1 | 10/2010 | Korb et al. |
| 2010/0259723 | A1* | 10/2010 | Korb et al. .................... 351/206 |
| 2011/0242482 | A1 | 10/2011 | Olsen |
| 2011/0273669 | A1 | 11/2011 | Abitbol et al. |

FOREIGN PATENT DOCUMENTS

WO    WO-0026614 A1    5/2000

OTHER PUBLICATIONS

Brennan N.A., et al., "Clinical Application of the Oxygen Transmissibility of Powered Contact Lenses," Clinical and Experimental Optometry, 1991, vol. 74 (6), pp. 212.
(Continued)

*Primary Examiner* — Huy K Mai
*Assistant Examiner* — Daniele Manikeu
(74) *Attorney, Agent, or Firm* — Abbott Medical Optics Inc.

(57) ABSTRACT

Disclosed herein is a method of calculating tear film lipid and aqueous layer thicknesses and/or corneal surface refractive index from interferometry data obtained from simultaneous measurements of the aqueous and lipid layers of the tear film along with a measurement of the corneal surface reflectance.

20 Claims, 11 Drawing Sheets

(56) References Cited

OTHER PUBLICATIONS

Fogt N., et al., "Interferometric Measurement of Tear Film Thickness by Use of Spectral Oscillations," Journal of Optical Society of America, 1998, vol. 15 (1), pp. 268-275.
Gardner et al., "Tear Film Thickness: Responsiveness to Potential Cognitive Demands", American Academy of Optometry, Tampa Dec. 2004, 1 page.
Geldis et al., "The Impact of Punctual Occulsion on Soft Contact Lends Wearing Comfort and the Tear Film," Eye and Contact Lens, pp. 261-265, 2008, vol. 34 (5).
Hecht E., et al., "Interference" in: Optics, Chapter 9, Addison-Wesley Publishing Company, 2002, pp. 426-428.
Hinel E., et al., "Concurrent interferometric Measures of Lipid Layer Thickness and Tear Film Thinning Before and After Application of Lipid Emulsion Drop", American Academy of Optometry, Anaheim Oct. 2008, 1 page.
International Preliminary Report on Patentability and Written Opinion for Application No. PCT/US08/062682, mailed on Nov. 10, 2009, 12 pages.
International Search Report and Written Opinion for Application No. PCT/US2012/067188, mailed on Jul. 2, 2013, 11 pages.
International Search Report for Application No. PCT/US08/062682, mailed on Nov. 5, 2008, 6 pages.
Kimball et al., Evaporation is the Primary Mechanism of Pre-Corneal Tear Film Thinning. [online], Oct. 2008 [retrieved on Feb. 25, 2009]. Retrieved from the Internet:<URL: http://www.aaopt.org/Submission/Search/SubmissionViewer.asp"SID=2>.
Kimball et al., Improving Interferometric Tear Thickness Measurements by Using Longer Wavelengths. [online], [retrieved on Feb. 25, 2009]. Retrieved from the Internet:<URL: http://www.aaopt.org/Submission/Search/SubmissionViewer.asp"SID=7>.
King S., et al., "Three Interferometric Methods For Measuring The Thickness Of Layers Of The Tear Film," Optometry and Vision Science, 1999, vol. 76 (1), pp. 19-32.
King S., et al., "Why does Dry Eye Affect Inferior Cornea More than Superior Cornea", American Academy of Optometry, 2002, pp. 1-2.
King-Smith et al., "In vivo Measurement of the Thickness of Human Corneal Endothelium and Descemets Membrane Using Interferometry, E-Abstract 157," Investigative Ophthalmology & Visual Science, 2002, vol. 43.
King-Smith. et. al., "Noninvasive Measurement of the Thickness of the Human Corneal Endothelium and Descemet's Membrane", American Academy of Optometry, Dec. 8, 2001, pp. 1-2.
King-Smith et al., "Roughness of the Corneal Surface by Interferometry", Association for Research in Vision and Ophthalmology, May 6, 2007, 1 page.
King-Smith et al., "The Thickness of the Human Precorneal Tear Film: Evidence from Reflection Spectra," Investigative & Visual Science, pp. 3348-3359, 2000, vol. 41 (11).
King-Smith et al., "The Thickness of the Tear Film," Current Eye Research, pp. 357-368, 2004, vol. 29 (4-5), Taylor & Francis Health Sciences.
King-Smith P., et al., Interferometric Analysis of Reflections from the Tear Film and Ocular Surface. [online], [retrieved on Feb. 25, 2009]. Retrieved from the Internet:<URL: http://www.aaopt.org/Submission/Search/SubmissionViewer.asp"SID=4>.
King-Smith P., et al., "Measurement of the Thickness of the Lipid Layer of the Tear Film Using Reflection Spectra," Association for Research in Vision and Ophthalmology, Inc., 2008, Grand Floridian A, Program 1540.
King-Smith P.E., et al., "A Tear Layer of Thickness 1.6 to 7.3 Micrometer Determined from Reflectance Spectra," Investigative Ophthalmology & Visual Science, 1998, vol. 39 (4), pp. 2446-B303.
King-Smith P.E., et al., "Can the Mucus Layer of the Tear Film be Deomstrated by Interferometry", Investigative Ophthalmology & Visual Science, 2004, vol. 45, pp. 1-2.
King-Smith P.E., et al., "Further Evidence that the Thickness of the Normal Human Tear Film is about 3 Micrometre," Investigative Ophthalmology & Visual Science, 2000, vol. 41 (4), pp. 337-B337.
King-Smith P.E., et al., "Interferometric Imaging of the Full Thickness of the Precorneal Tear Film," Journal of the Optical Society of America A, Optics, Image Science, and Vision, 2006, vol. 23 (9), pp. 2097-2104.
King-Smith P.E., et al., "Is the Thickness of the Tear Film About 40 Micrometre or About 3 Micrometre", Investigative Ophthalmology & Visual Science, 1999, vol. 40 (4), pp. 2876-B751.
King-Smith P.E., et al., "Measurement of Tear Film Thickness by Spectro-Photometry," Investigative Ophthalmology & Visual Science, 1996, vol. 37 (3), pp. 4984-B594.
King-Smith P.,et al., "Is Inferior Tear Film Thinner than Superior Tear Film", Investigative Ophthalmology & Visual Science, 2003, vol. 44, pp. 2476.
Korb D.R., et al., "Tear Film Lipid Layer Thickness as a Function of Blinking," Cornea, 1994, vol. 13 (4), pp. 354-359.
Korb D.R., et al., "The Effect of Two Novel Lubricant Eye Drops on Tear Film Lipid Layer Thickness in Subjects With Dry Eye Symptoms," Optometry and Vision Science, 2005, vol. 82 (7), pp. 494-601.
Kwon O., et al., "Rough Surface Interferometry at 10.6 Microm,"Applied Optics, 1980, vol. 19 (11), pp. 1862-1869.
Lira M., et al., "The Effect of Lens Wear on Refractive Index of Conventional Hydrogel and Silicone-hydrogel Contact Lenses: A Comparative Study,"Contact Lens & Anterior Eye, 2008, vol. 31 (2), pp. 89-94.
Nichols, et al., "Assessing Visual Parameters in Dry Eye Disease," Cornea and Contact Lens, [retrieved on Feb. 25, 2009]. Retrieved from the Internet:<URL: http://www.aaopt.org/Submissions.Search/SubmissionViewer.asp"SID=2>.
Nichols et al., "Lipid Layer Thickness and Tear Film Thinning Before and After Application of a Lipid Emulsion Drop,," Association for Research in Vision and Ophthalmoogy, 2008.
Nichols et al., "Tear Film Thickness and Thinning Rate Following a Six-Week Trial of 2% Diquafosol Tetrasodium vs. Placebo in Dry Eye Patients," 2006.
Nichols et al., "The Impact of Contact Lens Care Solutions on the Thickness of the Tear Film and Contact Lens,"Cornea, Clinical Sciences, pp. 825-832, 2005, vol. 24 (7).
Nichols J.J., et al., "Hydrogel Contact Lens Binding Induced by Contact Lens Rewetting Drops,"Optometry and Vision Science, 2008, vol. 85(4), pp. 236-240.
Nichols J.J., et al., "Thickness of the Pre- and Post-Contact Lens Tear Film Measured in Vivo by Interferometry," Investigative Ophthalmology & Visual Science, 2003, vol. 44 (1), pp. 68-77.
Nichols J.J., et al., "Thinning Rate of the Precorneal and Prelens Tear Films," Investigative Ophthalmology & Visual Science, 2005, vol. 46 (7), pp. 2353-2361.
Nicols et al, "Role of Lipid Layer as a Barrier to Pre-Lens Tear Film Thinning", American Academy of Optometry, Anaheim Oct. 25, 2008, 1 page.
Pillai H.P., et al., "Optical Modeling of a-Si:H Thin Film Solar Cells with Rough Interfaces", pp. 159-162.
Rakels J.H., "Influence of the Surface Height Distribution on the Total Integrated Scatter (TIS) Formula," Nanotechnology, 1996, vol. 7, pp. 43-46.
Schlote T., et al., "Marked Reduction and Distinct Patterns of Eye Blinking in Patients With Moderately Dry Eyes During Video Display Terminal Use," Graefe's Archive for Clinical and Experimental Ophthalmology, 2004, vol. 242 (4), pp. 306-312.
Tiffany J.M., et al., "Refractive Index of Meibomian and Other Lipids," Current Eye Research, 1986, vol. 5 (11), pp. 887-889.
Yap M., "Tear Break-up Time is Related to Blink Frequency," Acta Ophthalmologica, 1991, vol. 69 (1), pp. 92-94.
Zeman M., et al., "Optical Modeling of a-Si:H Solar Cells with Rough Interfaces: Effect of Back Contact and Interface Roughness," Journal of Applied Physics, 2000, vol. 88 (11), pp. 6436-6443.
Zhu H., et al., "A Mathematical Model for Ocular Tear and Solute Balance," Current Eye Research, 2005, vol. 30 (10), pp. 841-854.

* cited by examiner

METHOD FOR CALCULATING TEAR FILM LIPID AND AQUEOUS LAYER THICKNESSES AND CORNEAL SURFACE REFRACTIVE INDEX FROM INTERFEROMETRY DATA

This application is a continuation of U.S. patent application Ser. No. 13/310,026, filed Dec. 2, 2011, the contents of which is hereby incorporated in their entirety for all purposes as if fully set forth herein.

FIELD OF THE INVENTION

The invention relates to measurement and analysis of the ocular environment.

BACKGROUND OF THE INVENTION

Dry eye disease affects approximately 12 million people in the US. The integrity of the tear film lipid and aqueous layers is critical for proper tear film function and avoidance of dry eye. Wavelength-dependent optical interferometry has been used to simultaneously measure tear film lipid and aqueous layers thicknesses at a single point at the apex of the cornea over a period of time. Such measurements can be used to diagnose sub categories of dry eye from (a) either lipid or aqueous deficiencies, or (b) time-profile changes in lipid and aqueous layer thicknesses after a blink.

Accurate and precise determination of lipid and aqueous layer thicknesses are critical for proper diagnosis of dry eye sub categories. Previous lipid and aqueous layer thickness calculation methods using interferometry data were conducted separately. This was due to the large differences in layer thicknesses (aqueous: 1-5 microns, lipid: 20-120 nanometers), basing aqueous thickness calculations upon spectral interference oscillations and absence of spectral oscillations from the lipid layer.

The latter absence of spectral oscillations from the lipid layer presents a difficulty in calculating tear film lipid layer thickness. Thus, there is a need for improvement in the accurate and precise determination of the thickness of the lipid layer. This improvement would be beneficial to the physician, and would allow researchers to better design lubricant eye drops for dry eye patients with meibomian gland dysfunction (MGD). Improved measurement methods may also allow researchers to design more comfortable contact lens and lens care solutions for contact lens wearers. Contact lens wear adversely affects the tear film lipid layer, which is thought to be responsible for the thinner, less stable tear film and resulting dryness among contact lens wearers than non-lens wearers.

Lastly, there are no known non-invasive diagnostic methods in the art for measuring the refractive index of the corneal epithelium at the precise boundary of the aqueous layer and the anterior surface of the corneal epithelium, known as the corneal glycocalyx. Anterior corneal surface refractive index is believed to be a parametric measurement directly related to the structure of the glycocalyx. The glycocalyx is comprised of transmembrane mucins and the integrity of the corneal glycocalyx is believed to be required for tear film stability and prevention of dry eye. Having such a diagnostic tool would assist researchers in the diagnosis of dry eye and development of compositions which could assist or restore a patient's glycocalyx function. Simultaneous in vivo measurements of this interface, along with tear film aqueous and lipid layer measurements, all of which comprise the ocular environment, may prove to be of use in dry eye diagnosis or elucidating dry eye etiology or ocular effects of topically-applied solutions.

DETAILED DESCRIPTION

Figure 1:
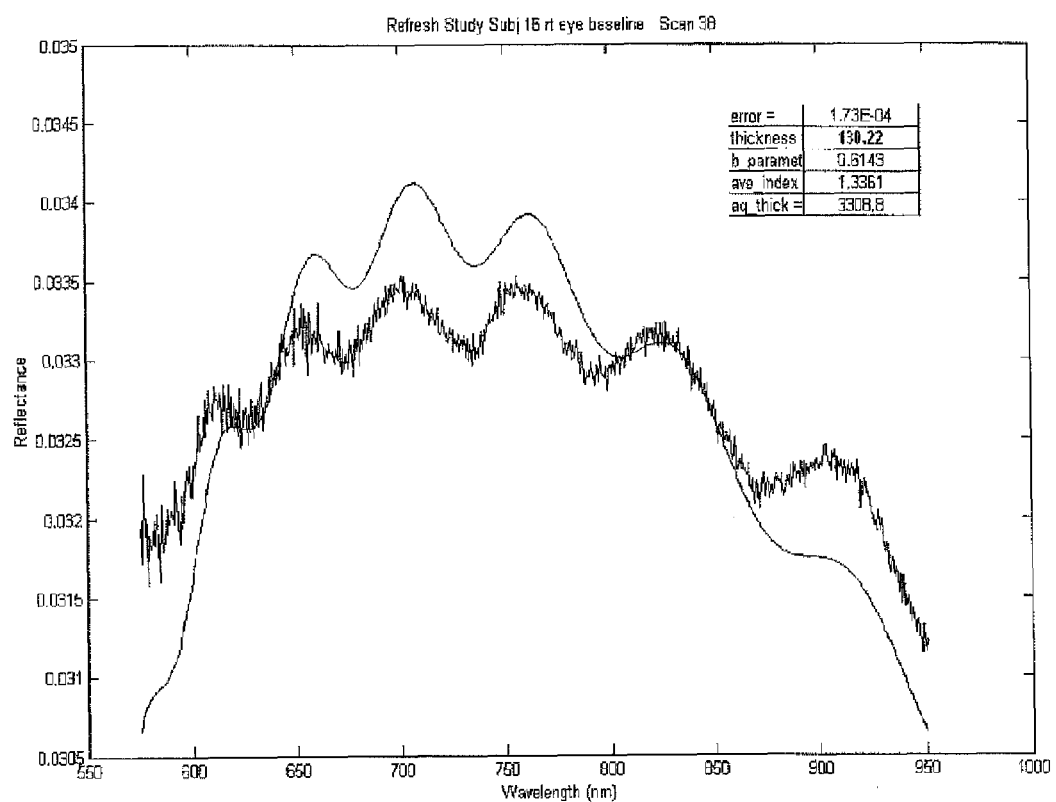
FIG. 1 shows a tear film spectrum fit (smooth line) before non-Gaussian corneal surface height correction. The 6 observed peaks are aqueous film spectral interference oscillations (3.309 microns). The large spectrum curvature is due to the lipid layer (130 nm).

This invention solves the problem of accurately and precisely measuring tear film lipid layer thickness by applying a new mathematical method to simultaneous tear film lipid and aqueous layer thicknesses and corneal refractive index calculations from interferometry data. The mathematical method is based upon electromagnetic and scalar scattering theories and thin film physics and includes two empirically-discovered factors, "bb" and "exp($-cc*1000/\lambda$)", wherein bb and cc are numbers, to account respectively for interferometer light losses/gains and light scattering at an optically rough surface.

The mathematical method for simultaneous tear film lipid and aqueous layers thicknesses and corneal refractive index calculations from interferometry data comprises the steps of: selecting a patient; aligning an eye of the patient with light originating from a light source; measuring tear film and ocular surface light reflectance of a patient; determining a value for tear film aqueous layer thickness, creating a mathematical construct of tear film and ocular surface light reflectance R based upon a characteristic mathematical matrix of a thin film stack comprising in sequence from top to bottom: air as a boundary, a tear film lipid layer, the tear film aqueous layer and a corneal epithelium as a semi-infinite substrate; multiplying R by two terms, bb and exp(-cc.*(1000./L).^1.0), wherein bb and cc are numbers, to find lipid and aqueous layer thicknesses and corneal surface refractive index and determining whether the tear film and ocular surface is deficient.

This new mathematical method provides a better determination of tear film lipid layer thickness than previous more empirical methods. This new method also provides a more accurate calculation of tear film aqueous layer thickness determination and provides for the first time a value for the corneal epithelial refractive index at the precise boundary of the aqueous layer and the surface of the corneal epithelium, believed to be the corneal glycocalyx. This new method requires one to take under consideration all of the optical characteristics of interferometry measurements and the tear film as well as the optical characteristics of the corneal epithelial surface, which forms the underlying substrate for the tear film. Using this method, a practitioner may determine whether the tear film meets acceptable parameters, or whether it is deficient in any way by comparison to a reference value. By way of example, but not of limitation, such deficiencies may include aqueous deficiencies, lipid deficiencies or deficiencies of the corneal surface. If the practitioner is a doctor, the deficiency may be treated by way of an appropriate medication. If the practitioner is a researcher, this deficiency may be noted as a way to steer research and/or development of a new medication.

Methods

A wavelength-dependent optical interferometer of the type developed by King-Smith et al and Huth (King-Smith P E, Fink B A, Fogt N, Nichols K K, Hill R M, Wilson G S. The thickness of the human precorneal tear film: evidence from reflection spectra. Invest Ophthalmol Vis Sci 2000; 41:3348-3359; Huth, U.S. Pat. No. 7,963,655 B2) was utilized. The tear film was modeled as a stack of 2 homogeneous films between air as a semi-infinite medium and the cornea as a semi-infinite substrate:

--- air ($n_0$)
lipid: 20-120 nm ($n_1$)
aqueous: 1-5 microns ($n_2$)
corneal epithelium ($n_3$)

---

The refractive indices, $n_n$, were derived from literature, where $n_0=1$,
$n_1$=sqrt(1+(((-851.03).*L.*L)./(L.*L-(816.139)))+(((420.267).*L.*L)./(L.*L-(-706.86)))+(((431.856).*L.*L)./(L.*L-(2355.29)))), derived from a Sellmeier equation fit of data from Tiffany (Tiffany, J M. Refractive index of meibomian and other lipids. Current Eye Research, 5 (11), 1986, 887-889),
$n_2$=1.32806+0.00306.*(1000./L).^2 from Ewen King-Smith, personal communication. and
$n_3$=b(2)+0.00306.*(1000./L).^2, where b(2) starting value=1.338 since the cornea refractive index at the aqueous tear interface is unknown ($n_3$ is expressed as v5 in software code, since it is a fitted term), and where
L=λ, nm for $n_1$, $n_2$ and $n_3$
There are a total of 3 boundaries at the interfaces between media of differing refractive indices:

Boundary I: between air and the lipid layer of the tear film
Boundary II: between the lipid and aqueous layers of the tear film
Boundary III: between the aqueous layer of the tear film and the corneal epithelium The angle of incidence θ onto the apex of the cornea of the incident light source in the interferometer was 0.091 radians. Other angles of refraction into a layer and incidence onto the succeeding layer are defined and expressed mathematically as follows from Snell's law:

$$n_o \sin \theta = n_1 \sin \beta;$$

$$n_1 \sin \beta = n_2 \sin \gamma \text{ and}$$

$$n_2 \sin \gamma = n_3 \sin \delta$$

and from the equations above for $n_0$, $n_1$, $n_2$ and $n_3$, and where:
angle of incident light onto the lipid layer, angle θ=0.091 radians;
angle of incident light onto the aqueous layer=angle β;
angle of incident light onto the corneal surface=angle γ and angle of refracted light into the cornea=angle δ.
Refracted light in the lipid layer=incidence angle onto the aqueous layer=angle β, where β=a sin($n_o$ sin θ/$n_1$)=a sin (1.*sin(0.091)./sqrt(1+(((-851.03).*L.*L)./(L.*L-(816.139)))+(((420.267).*L.*L)./(L.*L-(-706.86)))+(((431.856).*L.*L)./(L.*L-(2355.29)))));
Refracted light in the aqueous layer=incidence angle onto the corneal epithelium=angle γ, where γ=a sin($n_1$ sin β/$n_2$)=a sin($n_1$ sin(a sin($n_o$ sin θ/$n_1$)/$n_2$))=a sin (sqrt(1+(((-851.03).*L.*L)./(L.*L-(816.139)))+(((420.267).*L.*L)./(L.*L-(-706.86)))+(((431.856).*L.*L)./(L.*L-(2355.29)))).*sin(a sin(1.*sin(0.091)./sqrt(1+(((-851.03).*L.*L)./(L.*L-(816.139)))+(((420.267).*L.*L)./(L.*L-(-706.86)))+(((431.856).*L.*L)./(L.*L-(2355.29))))))./(1.32806+0.00306.*(1000./L).^2))); and
Refracted light in the corneal epithelium=angle δ, where δ=a sin($n_2$ sin γ/$n_3$)=a sin ((1.32806+0.00306.*(1000./L).^2).*sin(a sin(sqrt(1+(((-851.03).*L.*L)./(L.*L-(816.139)))+(((420.267).*L.*L)./(L.*L-(-706.86)))+(((431.856).*L.*L)./(L.*L-(2355.29)))).*sin(a sin(1.*sin(0.091)./sqrt(1+(((-851.03).*L.*L)./(L.*L-(816.139)))+(((420.267).*L.*L)./(L.*L-(-706.86)))+(((431.856).*L.*L)./(L.*L-(2355.29))))))./(1.32806+0.00306.*(1000./L).^2)))./(b(2)+0.00306.*(1000./L).^2)))). The last denominator here, (b(2)+0.00306.*(1000./L).^2), is expressed as v5 in software code, as the program needs to iteratively fit the best value of $n_3$ to the observed data and thus $n_3$ also becomes a determined output.

The film stack is first treated mathematically as in Hecht (Optics, Eugene Hecht, 4th ed., pp. 426-428, Pearson Education, Inc., Addison Wesley, 1301 Sanome St., San Francisco, Calif. 94111, 2002). Electric and magnetic field intensities are designated conventionally, as E and H, respectively, with subscripts I, II or III referring to these fields at the respective boundaries. Thus, for a single thin dielectric film (layer) between two semi-infinite transparent media, $$E_I = E_{II} \cos k_0 h + H_{II}(i \sin k_0 h)/\Omega_1$$

and $$H_I = E_{II}\Omega_1 i \sin k_0 h + H_{II} \cos k_0 h,$$

where $$\Omega_1 = \sqrt{\frac{\varepsilon_0}{\mu_0}} n_1 \cos\beta$$

and where h=2 $n_1$d cos β, where d=layer thickness.
In matrix notation, these linear equations take the form, $$\begin{bmatrix} E_I \\ H_I \end{bmatrix} = M \begin{bmatrix} E_{II} \\ H_{II} \end{bmatrix}$$

where, $$M = \begin{bmatrix} m_{11} & m_{12} \\ m_{21} & m_{22} \end{bmatrix} = \begin{bmatrix} \cos k_0 h & i\sin k_0 h/\Omega_1 \\ \Omega_1 i\sin k_0 h & \cos k_0 h \end{bmatrix}$$

Expansion of this equation using the values for $E_I$, $H_I$, $E_{II}$ and $H_{II}$ derived from the boundary condition requirements that the tangential components of both the electric and magnetic fields be equal across the boundaries yields the following expanded expression:

$$\begin{bmatrix} E_{i01} + E_{r01} + E_{t10} \\ (H_{i01} - (H_{r01} + H_{t10}))\Omega_0 \end{bmatrix} = \begin{bmatrix} m_{11} & m_{12} \\ m_{21} & m_{22} \end{bmatrix} \begin{bmatrix} E_{t12} \\ E_{t12}\Omega_2 \end{bmatrix}$$

Where $$\Omega_2 = \sqrt{\frac{\varepsilon_0}{\mu_0}} n_2 \cos\gamma$$

and $\Omega_0$ has its corresponding value based upon $n_0$ and cos θ, e.g., $\Omega_0 = \sqrt{(\varepsilon_0/\mu_0)} * n_0 \cos\theta$.
When the components of this matrix are expanded, one obtains the reflection (r) and transmission (t) coefficients:

$$r = \frac{E_{reflected\ total}}{E_{total}}$$
$$= \frac{E_{r01} + E_{t10}}{E_{i01}}$$
$$= \frac{\Omega_0 m_{11} + \Omega_0\Omega_2 m_{12} - m_{21} - \Omega_2 m_{22}}{\Omega_0 m_{11} + \Omega_0\Omega_2 m_{12} + m_{21} + \Omega_2 m_{22}}$$

$$t = \frac{E_{transmitted\ total}}{E_{total}}$$
$$= \frac{E_{t12}}{E_{i01}}$$
$$= \frac{2\Omega_0}{\Omega_0 m_{11} + \Omega_0\Omega_2 m_{12} + m_{21} + \Omega_2 m_{22}}$$

The characteristic matrix, M, above, also written as $M_I$, relates the fields at the two adjacent boundaries in the above system with a single film between two semi-infinite transparent media. If there are two overlying films on a substrate, e.g., the tear film lipid and aqueous layers on the corneal epithelial substrate, the resultant system matrix is calculated by multiplication of the individual matrices of the lipid and aqueous layers.
Thus, $$\begin{bmatrix} E_I \\ H_I \end{bmatrix} = \begin{bmatrix} M_I M_{II} * E_{III} \\ H_{III} \end{bmatrix}$$

-continued
Where $$M_I M_{II} = \begin{bmatrix} m_{11} & m_{12} \\ m_{21} & m_{22} \end{bmatrix}$$
$$= \begin{bmatrix} \cos k_0 h_1 & i\sin k_0 h_1/\Omega_1 \\ \Omega_1 i\sin k_0 h_1 & \cos k_0 h_1 \end{bmatrix} * \begin{bmatrix} \cos k_0 h_2 & i\sin k_0 h_2/\Omega_2 \\ \Omega_2 i\sin k_0 h_2 & \cos k_0 h_2 \end{bmatrix}$$

where $h_1$ (lipid layer 1)=2 $n_1 d_{lip} \cos\beta$, $h_2$ (aqueous layer 2)=2 $n_2 d_{aq} \cos\gamma$, where $d_{lip}$ is the thickness of the tear film lipid layer (expressed as "a" in software code), $d_{aq}$ is the thickness of the tear film aqueous layer (expressed as "d" in software code), where $\Omega_1$ and $\Omega_2$ have their previous definitions and where $k_0 = \pi/\lambda$. From this, reflectance is calculated from:
$R=|r|^2=|(\Omega_0 m_{11} + \Omega_0\Omega_3 m_{12} - m_{21} - \Omega_3 m_{22})/(\Omega_0 m_{11} + \Omega_0\Omega_3 m_{12} + m_{21} + \Omega_3 m_{22})|$, where $\Omega_2$ is replaced by $\Omega_3$, since our substrate is the corneal epithelium, and where $\Omega_3$ has its corresponding value based upon $n_3$ and cos δ, e.g., $\Omega_3 = \sqrt{(\varepsilon_0/\mu_0)} * n_3 \cos\delta$. Reflectance is a measure of the proportion of intensities rather than field amplitudes. Reflectance is calculated since measurements can only be made of intensities. Matrix terms $m_{11}$, $m_{12}$, $m_{21}$ and $m_{22}$ are calculated from standard matrix algebra as follows:

$$\begin{bmatrix} a & b \\ c & d \end{bmatrix} * \begin{bmatrix} e & f \\ g & h \end{bmatrix} = \begin{bmatrix} ae+bg & af+bh \\ ce+dg & cf+dh \end{bmatrix}$$

Thus, ae+bg=$m_{11}$; af+bh=$m_{12}$; ce+dg=$m_{21}$; and cf+dh=$m_{22}$.
An example of matrix term calculation and expansion follows. From matrix algebra, $m_{11}$=cos $k_0 h_1$*cos $k_0 h_2$+i sin $k_0 h_1/\Omega_1 * \Omega_2$ i sin $k_0 h_2$=cos((2.*π)./λ).*$n_1 d_{lip}$ cos β)*cos ((2.*π)./λ).*$n_2 d_{aq}$ cos γ+((i sin((2.*π)./λ).*$n_1 d_{lip}$ cos β)/($\sqrt{(\varepsilon_0/\mu_0)}$*$n_1$ cos β))*($\sqrt{(\varepsilon_0/\mu_0)}$*$n_2$ cos γ*i sin((2.*π)./λ).*$n_2 d_{aq}$ cos γ).
Thus, $\Omega_0 m_{11} = \sqrt{(\varepsilon_0/\mu_0)}*n_0$ cos θ.*cos((2.*π)./λ).*$n_1 d_{lip}$ cos β)*cos((2.*π)./λ).*$n_2 d_{aq}$ cos γ+$\sqrt{(\varepsilon_0/\mu_0)}$*$n_0$ cos θ.*((i sin ((2.*π)./λ).*$n_1 d_{lip}$ cos β)/($\sqrt{(\varepsilon_0/\mu_0)}$*$n_1$ cos β))*($\sqrt{(\varepsilon_0/\mu_0)}$*$n_2$ cos γ*i sin((2.*π)./λ).*$n_2 d_{aq}$ cos γ).
In the software code for calculating R=|r|$^2$, the equation for the first term, $\Omega_0 m_{11}$, is expanded using values and equations above for $n_0$, $n_1$, $n_2$, θ, β and γ to:

```
Ω₀m₁₁=((((((1.*cos(0.091)).*(cos((((2.*pi)./L).*sqrt(1+
(((−851.03).*L.*L)./(L.*L−
(816.139)))+(((420.267).*L.*L)./(L.*L−(−706.86)))+
(((431.856).*L.*L)./(L.*L−
(2355.29)))).*a.*cos(asin(1.*sin(0.091)./sqrt(1+
(((−851.03).*L.*L)./(L.*L−
(816.139)))+(((420.267).*L.*L)./(L.*L−(−706.86)))+
(((431.856).*L.*L)./(L.*L−
(2355.29))))))).*cos((((2.*pi)./L).*(1.32806+0.00306.*
(1000./L). 2).*d.*cos(asin(sqrt(1+
(((−851.03).*L.*L)./(L.*L−(816.139)))+
(((420.267).*L.*L)./(L.*L−(−
706.86)))+(((431.856).*L.*L)./(L.*L−(2355.29)))).*sin
(asin(1.*sin(0.091)./sqrt(1+(((−
851.03).*L.*L)./(L.*L−(816.139)))+
(((420.267).*L.*L)./(L.*L−(−
706.86)))+(((431.856).*L.*L)./(L.*L−
(2355.29))))))./(1.32806+0.00306.*(1000./L).^2)))))−
(((1.32806+0.00306.*(1000./L).^2).*cos(asin(sqrt(1+
(((−851.03).*L.*L)./(L.*L−
(816.139)))+(((420.267).*L.*L)./(L.*L−(−706.86)))+
(((431.856).*L.*L)./(L.*L−
(2355.29)))).*sin(asin(1.*sin(0.091)./sqrt(1+
(((−851.03).*L.*L)./(L.*L−
(816.139)))+(((420.267).*L.*L)./(L.*L−(−706.86)))+
```

-continued

```
(((431.856).*L.*L)./(L.*L−
(2355.29)))))))./(1.32806+0.00306.*(1000./L).^2))))./
(sqrt(1+(((−851.03).*L.*L)./(L.*L−
(816.139)))+(((420.267).*L.*L)./(L.*L−(−706.86)))+
(((431.856).*L.*L)./(L.*L−
(2355.29)))).*cos(asin(1.*sin(0.091)./sqrt(1+
(((−851.03).*L.*L)./(L.*L−
(816.139)))+(((420.267).*L.*L)./(L.*L−(−706.86)))+
(((431.856).*L.*L)./(L.*L−
(2355.29))))))).*sin((((2.*pi)./L).*(1.32806+0.00306.*
(1000./L).^2).*d.*cos(asin(sqrt(1+
(((−851.03).*L.*L)./(L.*L−(816.139)))+
(((420.267).*L.*L)./(L.*L−(−
706.86)))+(((431.856).*L.*L)./(L.*L−(2355.29)))).*sin
(asin(1.*sin(0.091)./sqrt(1+(((−
851.03).*L.*L)./(L.*L−(816.139)))+(((420.267).*L.*L)./
(L.*L−(−706.86)))+(((431.856).*L.*L)./(L.*L−
(2355.29)))))./(1.32806+0.00306.*(1000./L).^2))))).*sin
((((2.*pi)./L).*sqrt(1+(((−
851.03).*L.*L)./(L.*L−(816.139)))+(((420.267).*L.*L)./
(L.*L−(−706.86)))+(((431.856).*L.*L)./(L.*L−
(2355.29)))).*a.*cos(asin(1.*sin(0.091)./sqrt(1+(((−
851.03).*L.*L)./(L.*L−(816.139)))+(((420.267).*L.*L)./
(L.*L−(−706.86)))+(((431.856).*L.*L)./(L.*L−
(2355.29))))))))+(1.*cos(0.091)).*(v5.*cos(asin
((1.32806+0.00306.*(1000./L).^2).*sin(a
sin(sqrt(1+(((−851.03).*L.*L)./(L.*L−(816.139)))+
(((420.267).*L.*L)./(L.*L−(−
706.86)))+(((431.856).*L.*L)./(L.*L−(2355.29)))).*sin
(asin(1.*sin(0.091)./sqrt(1+(((−
851.03).*L.*L)./(L.*L−(816.139)))+(((420.267).*L.*L)./
(L.*L−(−706.86)))+(((431.856).*L.*L)./(L.*L−
(2355.29))))))./(1.32806+0.00306.*(1000./L).^2)))./v5))).
```

Other terms for calculating $R=|r|^2$ are calculated and expanded similarly, yielding the final equation:

```
R2=((((abs(((1.*cos(0.091)).*(cos((((2.*pi)./L).*
sqrt(1+(((−851.03).*L.*L)./(L.*L−
(816.139)))+(((420.267).*L.*L)./(L.*L−(−706.86)))+
(((431.856).*L.*L)./(L.*L−
(2355.29)))).*a.*cos(asin(1.*sin(0.091)./sqrt(1+
(((−851.03).*L.*L)./(L.*L−
(816.139)))+(((420.267).*L.*L)./(L.*L−(706.86)))+
(((431.856).*L.*L)./(L.*L−
(2355.29))))))).*cos((((2.*pi)./L).*(1.32806+
0.00306.*(1000./L).^2).*d.*cos(asin(sqrt(1+
(((−851.03).*L.*L)./(L.*L−(816.139)))+
(((420.267).*L.*L)./(L.*L−(−
706.86)))+(((431.856).*L.*L)./(L.*L−(2355.29)))).*
sin(asin(1.*sin(0.091)./sqrt(1+(((−
851.03).*L.*L)./(L.*L−(816.139)))+
(((420.267).*L.*L)./(L.*L−(−
706.86)))+(((431.856).*L.*L)./(L.*L−
(2355.29))))))./(1.32806+0.00306.*(1000./L).^2))))−
(((1.32806+0.00306.*(1000./L).^2).*cos(asin(sqrt(1+
(((−851.03).*L.*L)./(L.*L−
(816.139)))+(((420.267).*L.*L)./(L.*L−(−706.86)))+
(((431.856).*L.*L)./(L.*L−
(2355.29)))).*sin(asin(1.*sin(0.091)./sqrt(1+(((−
851.03).*L.*L)./(L.*L−
(816.139)))+(((420.267).*L.*L)./(L.*L−(−706.86)))+
(((431.856).*L.*L)./(L.*L−
(2355.29))))))./(1.32806+0.00306.*(1000./L).^2))))./
(sqrt(1+(((−851.03).*L.*L)./(L.*L−
(816.139)))+(((420.267).*L.*L)./(L.*L−(−706.86)))+
(((431.856).*L.*L)./(L.*L−
(2355.29)))).*cos(asin(1.*sin(0.091)./sqrt(1+
(((−851.03).*L.*L)./(L.*L−
(816.139)))+(((420.267).*L.*L)./(L.*L−(−706.86)))+
(((431.856).*L.*L)./(L.*L−
(2355.29))))))).*sin((((2.*pi)./L).*(1.32806+
0.00306.*(1000./L).^2).*d.*cos(asin(sqrt(1+
(((−851.03).*L.*L)./(L.*L−(816.139)))+
(((420.267).*L.*L)./(L.*L−(−
706.86)))+(((431.856).*L.*L)./(L.*L−(2355.29)))).*
sin(asin(1.*sin(0.091)./sqrt(1+(((−
```

```
851.03).*L.*L)./(L.*L−(816.139)))+
(((420.267).*L.*L)./(L.*L−(−
706.86)))+(((431.856).*L.*L)./(L.*L−
(2355.29))))))./(1.32806+0.00306.*(1000./L).^2)))).*
sin((((2.*pi)./L).*sqrt(1+(((−
851.03).*L.*L)./(L.*L−(816.139)))+
(((420.267).*L.*L)./(L.*L−(−
706.86)))+(((431.856).*L.*L)./(L.*L−
(2355.29)))).*a.*cos(asin(1.*sin(0.091)./sqrt(1+(((−
851.03).*L.*L)./(L.*L−(816.139)))+
(((420.267).*L.*L)./(L.*L−(−
706.86)))+(((431.856).*L.*L)./(L.*L−
(2355.29))))))))+(1.*cos(0.091)).*(v5.*cos(
asin((1.32806+0.00306.*(1000./L).^2).*sin(a
sin(sqrt(1+(((−851.03).*L.*L)./(L.*L−(816.139)))+
(((420.267).*L.*L)./(L.*L−(−
706.86)))+(((431.856).*L.*L)./(L.*L−(2355.29)))).*
sin(asin(1.*sin(0.091)./sqrt(1+(((−
851.03).*L.*L)./(L.*L−(816.139)))+
(((420.267).*L.*L)./(L.*L−(−
706.86)))+(((431.856).*L.*L)./(L.*L−
(2355.29))))))./(1.32806+0.00306.*
(1000./L).^2))))/v5))).*(−
i.*cos((((2.*pi)./L).*sqrt(1+(((−851.03).*L.*L)./(L.*L−
(816.139)))+(((420.267).*L.*L)./(L.*L−(−706.86)))+
(((431.856).*L.*L)./(L.*L−
(2355.29)))).*a.*cos(asin(1.*sin(0.091)./sqrt(1+
(((−851.03).*L.*L)./(L.*L−
(816.139)))+(((420.267).*L.*L)./(L.*L−(−706.86)))+
(((431.856).*L.*L)./(L.*L−
(2355.29))))))).*(sin((((2.*pi)./L).*(1.32806+
0.00306.*(1000./L).^2).*d.*cos(asin(sqrt(1+
(((−851.03).*L.*L)./(L.*L−(816.139)))+
(((420.267).*L.*L)./(L.*L−(−
706.86)))+(((431.856).*L.*L)./(L.*L−(2355.29)))).*
sin(asin(1.*sin(0.091)./sqrt(1+(((−
851.03).*L.*L)./(L.*L−(816.139)))+
(((420.267).*L.*L)./(L.*L−(−
706.86)))+(((431.856).*L.*L)./(L.*L−
(2355.29))))))./(1.32806+0.00306.*(1000./L).^2))))./
((1.32806+0.00306.*(1000./L).^2).
(((−851.03).*L.*L)./(L.*L−(816.139)))+
(((420.267).*L.*L)./(L.*L−(−
706.86)))+(((431.856).*L.*L)./(L.*L−(2355.29)))).*
sin(asin(1.*sin(0.091)./sqrt(1+(((−
851.03).*L.*L)./(L.*L−(816.139)))+
(((420.267).*L.*L)./(L.*L−(−
706.86)))+(((431.856).*L.*L)./(L.*L−
(2355.29))))))./(1.32806+0.00306.*(1000./L).+2)))))−
i.*cos((((2.*pi)./L).*(1.32806+0.00306.*
(1000./L).^2).*d.*cos(asin(sqrt(1+(((−
851.03).*L.*L)./(L.*L−(816.139)))+
(((420.267).*L.*L)./(L.*L−(−
706.86)))+(((431.856).*L.*L)./(L.*L−(2355.29)))).*
sin(asin(1.*sin(0.091)./sqrt(1+(((−
851.03).*L.*L)./(L.*L−(816.139)))+
(((420.267).*L.*L)./(L.*L−(−
706.86)))+(((431.856).*L.*L)./(L.*L−
(2355.29))))))./(1.32806+0.00306.*(1000./L).^2))))).*
(sin((((2.*pi)./L).*sqrt(1+(((−
851.03).*L.*L)./(L.*L−(816.139)))+
(((420.267).*L.*L)./(L.*L−(−
706.86)))+(((431.856).*L.*L)./(L.*L−(2355.29)))).*a.*
cos(asin(1.*sin(0.091)./sqrt(1+(((−
851.03).*L.*L)./(L.*L−(816.139)))+
(((420.267).*L.*L)./(L.*L−(−
706.86)))+(((431.856).*L.*L)./(L.*L−(2355.29))))))))./
(sqrt(1+(((−851.03).*L.*L)./(L.*L−
(816.139)))+(((420.267).*L.*L)./(L.*L−(−706.86)))+
(((431.856).*L.*L)./(L.*L−
(2355.29)))).*cos(asin(1.*sin(0.091)./sqrt(1+
(((−851.03).*L.*L)./(L.*L−
(816.139)))+(((420.267).*L.*L)./(L.*L−(−706.86)))+
(((431.856).*L.*L)./(L.*L−
(2355.29)))))))))−(−(sqrt(1+
(((−851.03).*L.*L)./(L.*L−
(816.139)))+(((420.267).*L.*L)./(L.*L−(−706.86)))+
(((431.856).*L.*L)./(L.*L−
(2355.29)))).*cos(asin(1.*sin(0.091)./sqrt(1+
```

-continued (((−851.03).*L.*L)./(L.*L−(816.139))+(((420.267).*L.*L)./(L.*L−(−706.86)))+(((431.856).*L.*L)./(L.*L−(2355.29)))))).*i.*sin((((2.*pi)./L).*sqrt(1+(((−851.03).*L.*L)./(L.*L−(816.139))+(((420.267).*L.*L)./(L.*L−(−706.86)))+(((431.856).*L.*L)./(L.*L−(2355.29)))).*a.*cos(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29)))))).*cos((((2.*pi)./L).*(1.32806+0.00306.*(1000./L).^2).*d.*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2))))−cos((((2.*pi)./L).*sqrt(1+(((−851.03).*L.*L)./(L.*L−(816.139))+(((420.267).*L.*L)./(L.*L−(−706.86)))+(((431.856).*L.*L)./(L.*L−(2355.29)))).*a.*cos(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))).*((1.32806+0.00306.*(1000./L).^2).*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2)))).*i.*sin((((2.*pi)./L).*(1.32806+0.00306.*(1000./L).^2).*d.*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2))))−(v5.*cos((1.32806+0.00306.*(1000./L).^2).*sin(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L).4.*L−(−706.86)))+(((431.856).*L.*L)./(L.*L−(2355.29))))))./(1.32806+0.00306.*(1000./L).^2)))./v5))).*(cos((((2.*pi)./L).*sqrt(1+(((−851.03).*L.*L)./(L.*L−(816.139))+(((420.267).*L.*L)./(L.*L−(−706.86)))+(((431.856).*L.*L)./(L.*L−(2355.29)))).*a.*cos(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))).*cos((((2.*pi)./L).*(1.32806+0.00306.*(1000./L).^2).*d.*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2))))−((sqrt(1+(((−851.03).*L.*L)./(L.*L−

(816.139)))+(((431.856).*L.*L)./(L.*L−(−706.86)))+(((431.856).*L.*L)./(L.*L−(2355.29))).*cos(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29)))))))./((1.32806+0.00306.*(1000./L).^2).*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2)))).*sin((((2.*pi)./L).*sqrt(1+(((−851.03).*L.*L)./(L.*L−(816.139))+(((420.267).*L.*L)./(L.*L−(−706.86)))+(((431.856).*L.*L)./(L.*L−(2355.29)))).*a.*cos(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29)))))))).*sin((((2.*pi)./L).*(1.32806+0.00306.*(1000./L).^2).*d.*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2)))))./((1.*cos(0.091)).*(cos((((2.*pi)./L).*sqrt(1+(((−851.03).*L.*L)./(L.*L−(816.139))+(((420.267).*L.*L)./(L.*L−(−706.86)))+(((431.856).*L.*L)./(L.*L−(2355.29)))).*a.*cos(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))).*cos((((2.*pi)./L).*(1.32806+0.00306.*(1000./L).^2).*d.*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2))))−(((1.32806+0.00306.*(1000./L).^2).*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2))))./(sqrt(1+(((−851.03).*L.*L)./(L.*L−(816.139))+(((420.267).*L.*L)./(L.*L−(−706.86)))+(((431.856).*L.*L)./(L.*L−(2355.29)))).*cos(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29)))))).*sin((((2.*pi)./L).*(1.32806+0.00306.*(1000./L).^2).*d.*cos(asin(sqrt(1+(((−851.03).*L.*L)./(L.*L−(816.139))+(((420.267).*L.*L)./(L.*L−(−706.86)))+(((431.856).*L.*L)./(L.*L−(2355.29)))).*sin(asin(1.*sin(0.091)./sqrt(1+(((−851.03).*L.*L)./(L.*L−(816.139))+(((420.267).*L.*L)./(L.*L−(−706.86)))+(((431.856).*L.*L)./(L.*L−(2355.29))))))./(1.32806+0.00306.*(1000./L).^2))).*sin((((2.*pi)./L).*sqrt(1+(((−

-continued

```
851.03).*L.*L)./(L.*L-(816.139)))+
(((420.267).*L.*L)./(L.*L-(-
706.86)))+(((431.856).*L.*L)./(L.*L-(2355.29)))).*
a.*cos(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))))+(1.*cos(0.091)).*(v5.*cos(asin
((1.32806+0.00306.*(1000./L).^2).*sin(a
sin(sqrt(1+(((-851.03).*L.*L)./(L.*L-(816.139)))+
(((420.267).*L.*L)./(L.*L-(-
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*
(1000./L).^2))).*(-
i.*cos((((2.*pi)./L).*sqrt(1+(((-851.03).*L.*L)./(L.*L-
(816.139)))+(((420.267).*L.*L)./(L.*L-(-706.86)))+
(((431.856).*L.*L)./(L.*L-
(2355.29)))).*a.*cos(asin(1.*sin(0.091)./sqrt(1+
(((-851.03).*L.*L)./(L.*L-
(816.139)))+(((420.267).*L.*L)./(L.*L-(-706.86)))+
(((431.856).*L.*L)./(L.*L-
(2355.29)))))))).*(sin((((2.*pi)./L).*(1.32806+
0.00306.*(1000./L).^2).*d.*cos(asin(sqrt(1+
(((-851.03).*L.*L)./(L.*L-(816.139)))+
(((420.267).*L.*L)./(L.*L-(-
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*(1000./L).^2)))))./
((1.32806+0.00306.*(1000./L).^2).
*cos(asin(sqrt(1+(((-851.03).*L.*L)./(L.*L-
(816.139)))+(((420.267).*L.*L)./(L.*L+
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*(1000./L).^2))))-
i.*cos((((2.*pi)./L).*(1.32806+0.00306.*
(1000./L).^2).*d.*cos(asin(sqrt(1+(((-
851.03).*L.*L)./(L.*L-(816.139)))+
(((420.267).*L.*L)./(L.*L-(-
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*(1000./L).^2)))).*
sin((((2.*pi)./L).*sqrt(1+(((-
851.03).*L.*L)./(L.*L-(816.139)))+
(((420.267).*L.*L)./(L.*L-(-
706.86)))+(((431.856).*L.*L)./(L.*L-(2355.29)))).*
a.*cos(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-(2355.29))))))))./
(sqrt(1+(((-851.03).*L.*L)./(L.*L-
(816.139)))+(((420.267).*L.*L)./(L.*L-(-706.86)))+
(((431.856).*L.*L)./(L.*L-
(2355.29)))).*cos(asin(1.*sin(0.091)./sqrt(1+
(((-851.03).*L.*L)./(L.*L-
(816.139)))+(((420.267).*L.*L)./(L.*L-(-706.86)))+
(((431.856).*L.*L)./(L.*L-
(2355.29))))))))+(-(sqrt(1+(((-851.03).*L.*L)./(L.*L-
(816.139)))+(((420.267).*L.*L)./(L.*L-(-706.86)))+
(((431.856).*L.*L)./(L.*L-
(2355.29)))).*cos(asin(1.*sin(0.091)./sqrt(1+
(((-851.03).*L.*L)./(L.*L-
(816.139)))+(((420.267).*L.*L)./(L.*L-(-706.86)))+
(((431.856).*L.*L)./(L.*L-
(2355.29))))))).*i.*sin((((2.*pi)./L).*sqrt(1+
(((-851.03).*L.*L)./(L.*L-
(816.139)))+(((420.267).*L.*L)./(L.*L-(-706.86)))+

(((431.856).*L.*L)./(L.*L-
(2355.29)))).*a.*cos(asin(1.*sin(0.091)./sqrt(1+
(((-851.03).*L.*L)./(L.*L-
(816.139)))+(((420.267).*L.*L)./(L.*L-(-706.86)))+
(((431.856).*L.*L)./(L.*L-
(2355.29)))))))).*cos((((2.*pi)./L).*(1.32806+
0.00306.*(1000./L).^2).*d.*cos(asin(sqrt(1+
(((-851.03).*L.*L)./(L.*L-(816.139)))+
(((420.267).*L.*L)./(L.*L-(-
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*(1000./L).^2))))-
cos((((2.*pi)./L).*sqrt(1+(((-
851.03).*L.*L)./(L.*L-(816.139)))+
(((420.267).*L.*L)./(L.*L-(-
706.86)))+(((431.856).*L.*L)./(L.*L-(2355.29)))).*
a.*cos(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29)))))))).*(1.32806+0.00306.*(1000./L).^2).*
cos(asin(sqrt(1+(((-
851.03).*L.*L)./(L.*L-(816.139)))+
(((420.267).*L.*L)./(L.*L-(-
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*(1000./L).^2)))).*
i.*sin((((2.*pi)./L).*(1.32806+0.003
06.*(1000./L).^2).*d.*cos(asin(sqrt(1+
(((-851.03).*L.*L)./(L.*L-
(816.139)))+(((420.267).*L.*L)./(L.*L-(-706.86)))+
(((431.856).*L.*L)./(L.*L-
(2355.29)))).*sin(asin(1.*sin(0.091)./sqrt(1+
(((-851.03).*L.*L)./(L.*L-
(816.139)))+(((420.267).*L.*L)./(L.*L-(-706.86)))+
(((431.856).*L.*L)./(L.*L-
(2355.29))))))./(1.32806+0.00306.*(1000./L).^2))))+
(v5.*cos(asin((1.32806+0.00306.*
(1000./L).^2).*sin(asin(sqrt(1+
(((-851.03).*L.*L)./(L.*L-
(816.139)))+(((420.267).*L.*L)./(L.*L-(-706.86)))+
(((431.856).*L.*L)./(L.*L-
(2355.29)))).*sin(asin(1.*sin(0.091)./sqrt(1+
(((-851.03).*L.*L)./(L.*L-
(816.139)))+(((420.267).*L.*L)./(L.*L-(-706.86)))+
(((431.856).*L.*L)./(L.*L-
(2355.29))))))./(1.32806+0.00306.*
(1000./L).^2)))./v5))).*
(cos((((2.*pi)./L).*sqrt(1+(((-
851.03).*L.*L)./(L.*L-(816.139)))+
(((420.267).*L.*L)./(L.*L-(-
706.86)))+(((431.856).*L.*L)./(L.*L-(2355.29)))).*
a.*cos(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29)))))))).*cos((((2.*pi)./L).*(1.32806+
0.00306.*(1000./L).^2).*d.*cos(asin(sqrt(1+
(((-851.03).*L.*L)./(L.*L-(816.139)))+
(((420.267).*L.*L)./(L.*L-(-
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*(1000./L).^2))))-
((sqrt(1+(((-851.03).*L.*L)./(L.*L-
(816.139)))+(((420.267).*L.*L)./(L.*L-(-706.86)))+
(((431.856).*L.*L)./(L.*L-
(2355.29))).*cos(asin(1.*sin(0.091)./sqrt
(1+(((-851.03).*L.*L)./(L.*L-
(816.139)))+(((420.267).*L.*L)./(L.*L-(-706.86)))+
(((431.856).*L.*L)./(L.*L-+
```

-continued

```
(2355.29))))))./((1.32806+0.00306.*(1000./L).^2).*
cos(asin(sqrt(1+(((-
(((851.03).*L.*L)./(L.*L-(816.139)))+
(((420.267).*L.*L)./(L.*L-(-
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*(1000./L).^2))))).*
sin((((2.*pi)./L).*sqrt(1+(((-
851.03).*L.*L)./(L.*L-(816.139)))+
(((420.267).*L.*L)./(L.*L-(-
706.86)))+(((431.856).*L.*L)./(L.*L-(2355.29)))).*
a.*cos(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))).*sin((((2.*pi)./L).*(1.32806+0.00306.*
(1000./L).^2).*d.*cos(asin(sqrt(1+
(((-851.03).*L.*L)./(L.*L-(816.139)))+
(((420.267).*L.*L)./(L.*L-(-
706.86)))+(((431.856).*L.*L)./(L.*L-(2355.29)))).*
sin(asin(1.*sin(0.091)./sqrt(1+(((-
851.03).*L.*L)./(L.*L-(816.139)))+
(((420.267).*L.*L)./(L.*L-(-
706.86)))+(((431.856).*L.*L)./(L.*L-
(2355.29))))))./(1.32806+0.00306.*(1000./L).^2
)))))))). 2))).*bb.*exp(-cc.*(1000./L).^1.0);
```

The final equation and software require that an initial value for tear film aqueous layer thickness be used. This initial value for tear film aqueous layer thickness can be derived from methods disclosed in U.S. Pat. No. 7,963,655 B2, which is incorporated herein by reference. Alternatively, since the aqueous layer thickness of the tear film averages about 3000 nm for non-contact lens wearers, this can be used as an input starting value for non-contact lens wearers. Since the aqueous layer thickness of the tear film averages about 2500 nm for contact lens wearers, this can be used as an input starting value for contact lens wearers.

Note the final equation also includes two additional terms, bb and $\exp(-cc.*(1000./L).^{1.0})$, wherein bb and cc are numbers, not described by the theory for the characteristic matrix for a film stack. The first term, bb, was determined to be required to increase or decrease the mathematically-fitted reflectance, R, at each measured wavelength, to achieve a better fit to measured reflectance. This is necessary since the interferometer measures only relative reflectance of the tear film, relative to the measured reflectance of a glass lens standard, not absolute reflectance. Thus, interferometer instrument raw data are quotients of measured reflectance of the tear film divided by the measured reflectance of the glass lens standard. Measured tear film reflectance is subject to changes in light intensity, depending upon focus and eye alignment, since the instrument is designed to reflect only a small spot of light from the apex of the cornea.

The second term, $\exp(-cc.*(1000./L).^{1.0})$, was discovered empirically to achieve a better fit of the measured reflectance data to the mathematically-fitted reflectance, R, at each measured wavelength, L. This term evolved from an initial failed attempt to use scalar light scattering theory and a theoretical Gaussian distribution of substrate (e.g., the corneal epithelium in our case) surface height variation, which involved multiplying R by $\exp(-cc.*(1000./L).^{2.0})$. Scalar scattering theory is based upon the principle that longer light wavelengths are scattered by a rough surface less than shorter wavelengths, resulting in interference peak and trough amplitude modulation. In other words, interference spectra of thin films overlying rough surfaces are expected to have larger oscillations at longer wavelengths, due to variation of thickness of the thin film layer caused by variation of surface roughness (height) of the underlying surface.

We believe, without wishing to be bound by this explanation, that the second term, $\exp(-cc.*(1000./L).^{1.0})$, accounts for an empirically-discovered non-Gaussian distribution of substrate surface roughness. This is believed due to the macroscopic size of the imaged area of the tear film (12.5×133 um) which would encompass multiple corneal epithelial cell surfaces, cell borders and corneal surface microplicae.

In some cases, a second term to account for substrate surface roughness of $\exp(-a(1000/\lambda)+b(1000/\lambda)^2)$, wherein a and b are numbers, was found to provide a better fit of the measured reflectance data to the mathematically-fitted reflectance, R. The format of this second term accounts for both non-Gaussian and Gaussian distributions in surface roughness. It is anticipated that other non-Gaussian surface roughness distributions will have to be accounted-for when using the methods of the present invention. Such surface roughness distributions can be mathematically modeled using mathematics terms as in Rakels J. Influence of the surface height distribution on the total integrated scatter (TIS) formula. *Nanotechnology* 7 (1996): 43-46, which is incorporated herein in its entirety by reference. Alternatively, any non-Gaussian height distribution function or single mathematical term may be employed, whose relevance can be determined by the goodness of fit methods of the present invention, comparing a fitted function R comprising a non-Gaussian height distribution function or single mathematical term to experimentally measured interference spectra.

Given the length of the equation, changing wavelength and requirements for fitting calculated R to measured R, a least squares minimization technique is preferably employed, where an error function is evaluated and minimized. Software was developed using the MatLab® software platform from The MathWorks, Inc. The software of the present invention uses the Gauss-Newton method to find the optimal values for the refractive index of the corneal epithelium, thickness of the lipid layer and "bb" and "cc" parameters. The software requires starting values for aqueous layer thickness, lipid layer thickness (using a value selected from 20 to 140 nm), refractive index of the corneal epithelium (starting with $1.338+0.00306.*(1000./L).^{2}$) and bb parameter (set=1 to start). Other fitting-error minimization methods other than the Gauss-Newton method may also be employed, which are well-known in the art, such as the Levenberg-Marquardt algorithm.

Thus, the mathematical method for simultaneous tear film lipid and aqueous layers thicknesses and corneal refractive index calculations from interferometry data comprises the steps of: selecting a patient; aligning an eye of the patient with light from a light source; measuring tear film and ocular surface light reflectance of a patient; determining a value for tear film aqueous layer thickness, fitting the light reflectance from the eye of the patient to a mathematical construct of tear film and ocular surface light reflectance R based upon a characteristic mathematical matrix of a thin film stack comprising in sequence from top to bottom: air as a boundary, a tear film lipid layer, the tear film aqueous layer and a corneal epithelium as a semi-infinite substrate; multiplying R by two terms, bb and $\exp(-cc.*(1000/L).^{1.0})$, wherein bb and cc are numbers, to find lipid and aqueous layer thicknesses and conical surface refractive index and determining whether the tear film and ocular surface is deficient by comparing the obtained thickness and refractive index values to reference values representing a normal eye without any deficiencies or an eye with deficiencies.

Alternatively, depending on the patient being tested, since the aqueous layer thickness of the tear film in non-contact lens wearers averages about 3000 nm, this can be used as an input starting value and the step for determining a value for aqueous layer thickness in the method above can be omitted.

Alternatively, depending on the patient being tested, since the aqueous layer thickness of the tear film in contact lens wearers averages about 2500 am, this can be used as an input starting value and the step for determining a value for aqueous layer thickness in the method above can be omitted.

Also, if interferometer instrument optical reflectance measurement errors are eliminated, the bb term becomes 1, and thus can be omitted.

This new method provides a value for the conical epithelial refractive index at the precise boundary of the aqueous layer and the surface of the corneal epithelium, believed to be the corneal glycocalyx. The glycocalyx is comprised of the membrane-spanning mucin MUC16. When MUC16 is lost or shed, a dry spot can form. Since the integrity of the corneal glycocalyx is known to be required for tear film stability and prevention of dry eye, this new method offers a potential new diagnostic tool for the diagnosis of dry eye.

This new method can be used for both non-contact lens wearers and contact lens wearers. The method can be used to evaluate the efficacy and retention time of novel lubricant eye drops such as those based upon oil-in-water emulsions and which are designed to supplement the lipid or lipid and aqueous layers of the tear film.

The following examples illustrate the method of the invention:

Example 1

Figure 2:
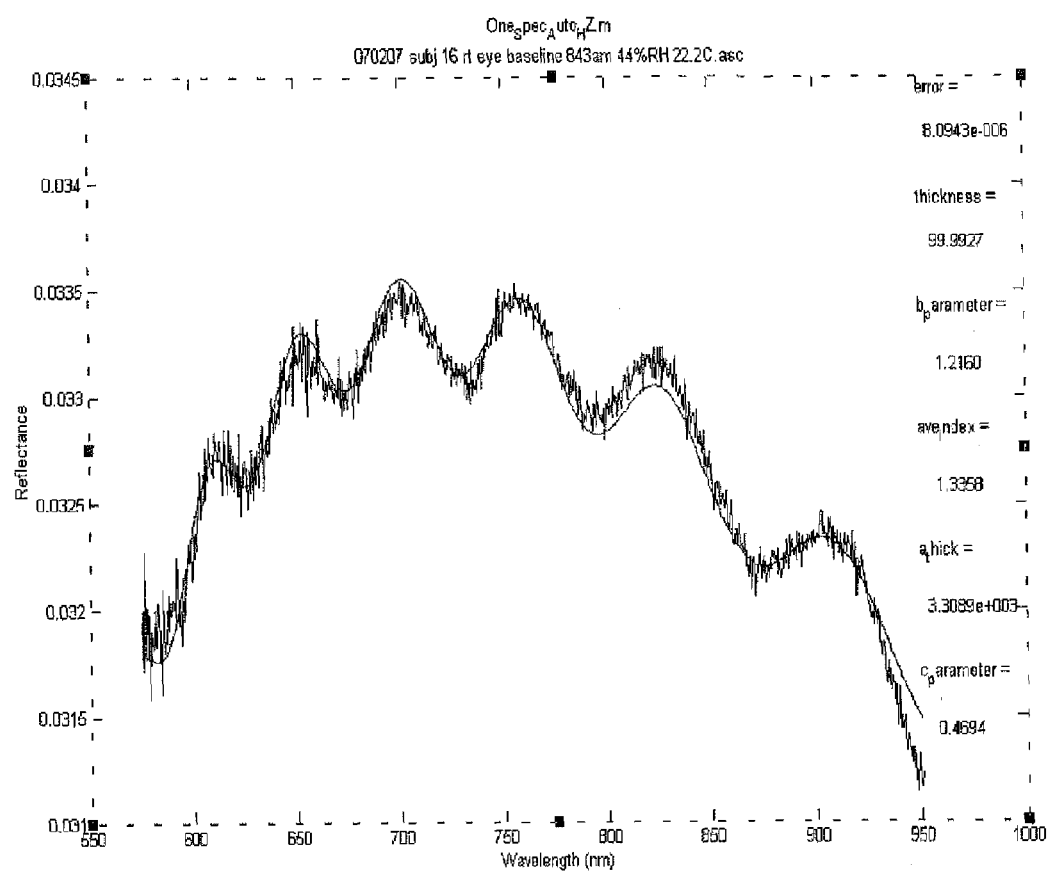
FIG. 2 shows a tear film spectrum fit (smooth line) after non-Gaussian corneal surface height correction with the (exp($-cc*1000/\lambda$)) term, wherein cc is a number representing a fitted parameter proportional to average surface roughness (height). Lipid=100 nm, aqueous=3.309 microns.

An interferometric reflectance spectrum of a human subject's right eye baseline tear film is taken, as described in U.S. Pat. No. 7,963,655 B2. Measured reflectance data are processed according to the method of the present invention without and with the application of the correction with the (exp (−cc*10001×)) term in the equation for total reflectance, R, wherein cc is a number. FIGS. 1 and 2 show the calculated tear film reflectance spectrum fits in smooth lines compared to the interferometer measured reflectance spectra in the lines with noise (small changes in measured reflectance observed as vertical lines). FIG. 1 shows that application of the method of the invention without the (exp (−cc*1000/λ)) term in the equation for total reflectance, R, results in a poor fit of the calculated tear film reflectance spectrum (smooth line) to that of the measured reflectance spectrum (line with noise). The lipid layer thickness is calculated to be 130 nm in this case. FIG. 2 shows that application of the method of the invention with the (exp (−cc*1000/λ)) term in the equation for total reflectance, R, results in an excellent fit of the calculated tear film reflectance spectrum (smooth line) to that of the measured reflectance spectrum (line with noise). The lipid layer thickness is calculated to be 100 nm in this case. Aqueous layer thickness is the same in both cases, 3.309 microns. These lipid and aqueous layer thickness values are considered to be within the range of values considered non-deficient. Calculations for the refractive index of the corneal epithelium are essentially the same in both cases, 1.3361 and 1.3358 respectively, for FIGS. 1 and 2. The (exp (−cc*1000/λ)) term accounts for a hypothetical non-Gaussian distribution in corneal surface roughness. This is believed due to the macroscopic size of the imaged area of the tear film (12.5×133 microns) and the variation of thickness of the aqueous layer caused by the variation of surface roughness (height) of the corneal surface.

Example 2

Figure 3:
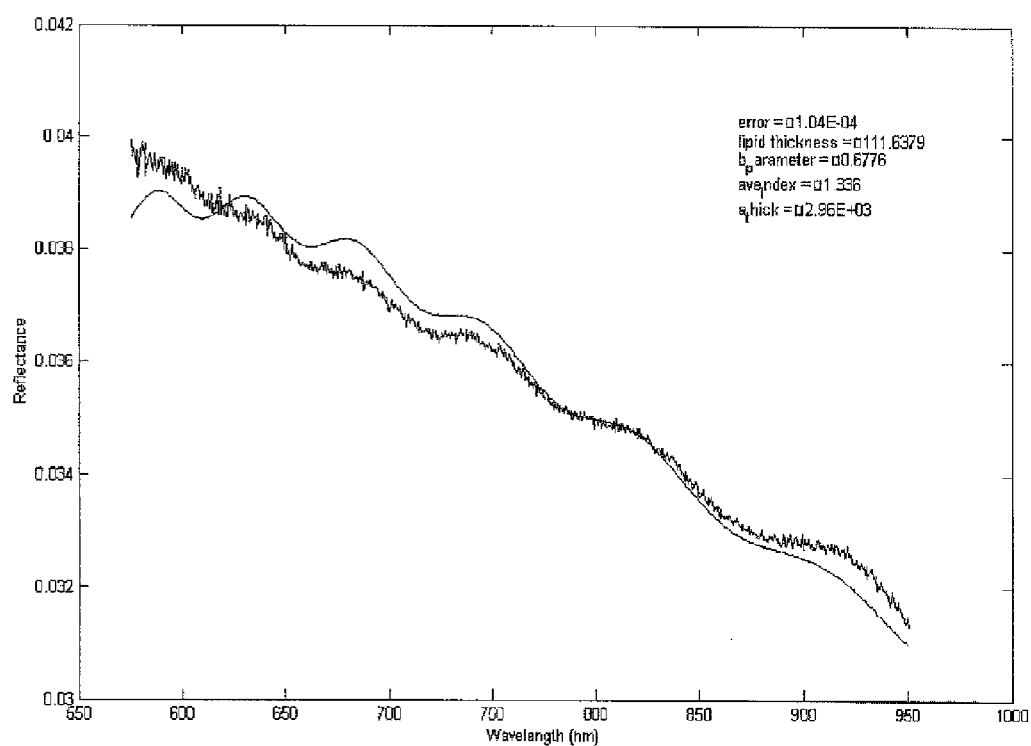
FIG. 3 shows the calculated tear film reflectance spectrum fit in smooth line compared to the interferometer measured reflectance spectrum in the lines with noise without the (exp($-cc*1000/\lambda$)) term in the equation for total reflectance.
Figure 4:
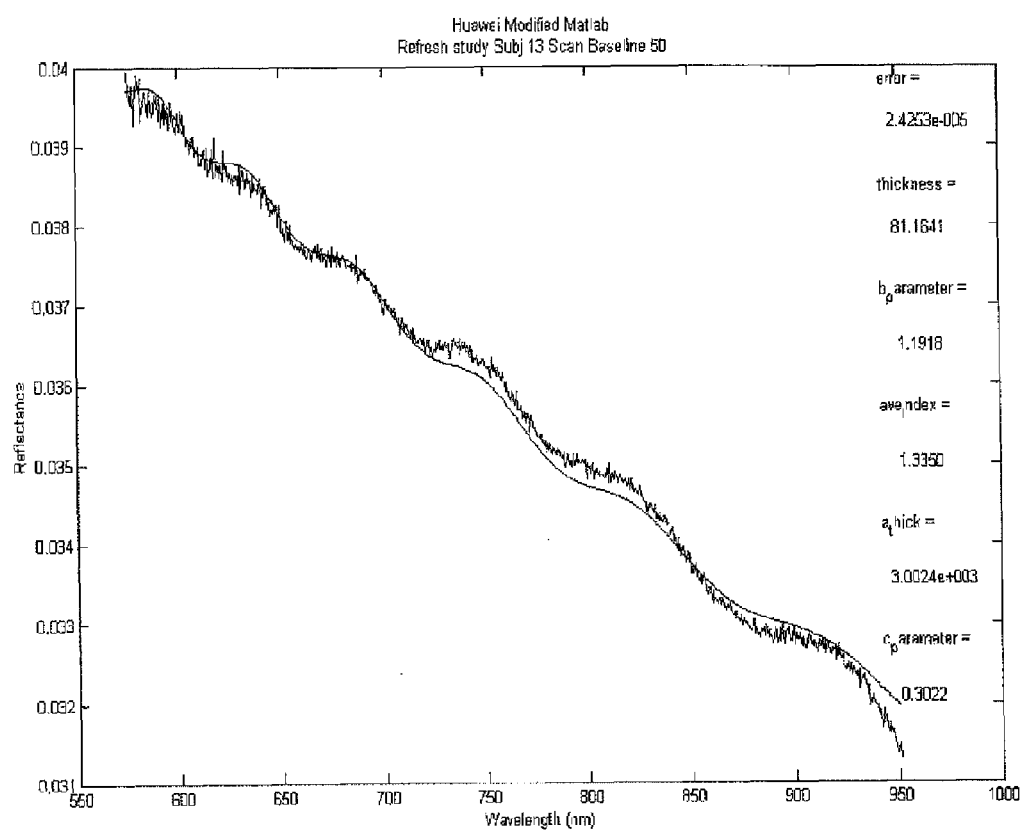
FIG. 4 shows the calculated tear film reflectance spectrum fit in smooth line compared to the interferometer measured reflectance spectrum in the lines with noise with the (exp($-cc*1000/\lambda$)) term in the equation for total reflectance.

An interferometric reflectance spectrum of a human subject's right eye baseline tear film is taken, as described in U.S. Pat. No. 7,963,655 B2. Measured reflectance data are processed according to the method of the present invention without and with the application of the correction with the (exp (−cc*1000/λ)) term in the equation for total reflectance, R. FIGS. 3 and 4 show the calculated tear film reflectance spectrum fits in smooth lines compared to the interferometer measured reflectance spectra in the lines with noise. FIG. 3 shows that application of the method of the invention without the (exp (−cc*1000/λ)) term in the equation for total reflectance, R, results in a poor fit of the calculated tear film reflectance spectrum (smooth line) to that of the measured reflectance spectrum (line with noise). The lipid layer thickness is calculated to be 111 nm in this case. FIG. 4 shows that application of the method of the invention with the (exp (−cc*1000/λ)) term in the equation for total reflectance, R, results in an excellent fit of the calculated tear film reflectance spectrum (smooth line) to that of the measured reflectance spectrum (line with noise). The lipid layer thickness is calculated to be 81 nm in this case. Aqueous layer thicknesses are similar in both cases, 2.96 and 3.002 microns respectively, for FIGS. 3 and 4. These lipid and aqueous layer thickness values are considered to be within the range of values considered non-deficient. Calculations for the refractive index of the corneal epithelium are close in both cases, 1.336 and 1.3350 respectively, for FIGS. 3 and 4.

Example 3

Figure 5:
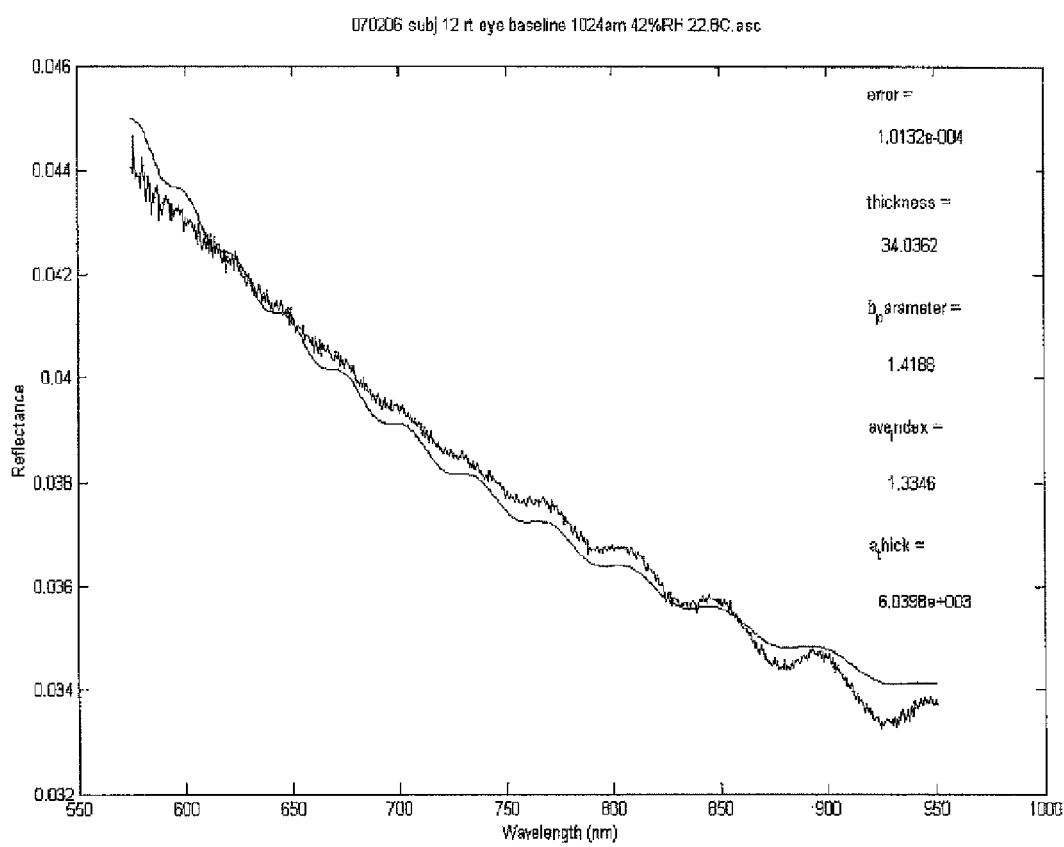
FIG. 5 shows the calculated tear film reflectance spectrum fit (smooth line) compared to the interferometer measured reflectance spectrum (line with noise) without the (exp($-cc*1000/\lambda$) term in the equation for total reflectance.
Figure 6:
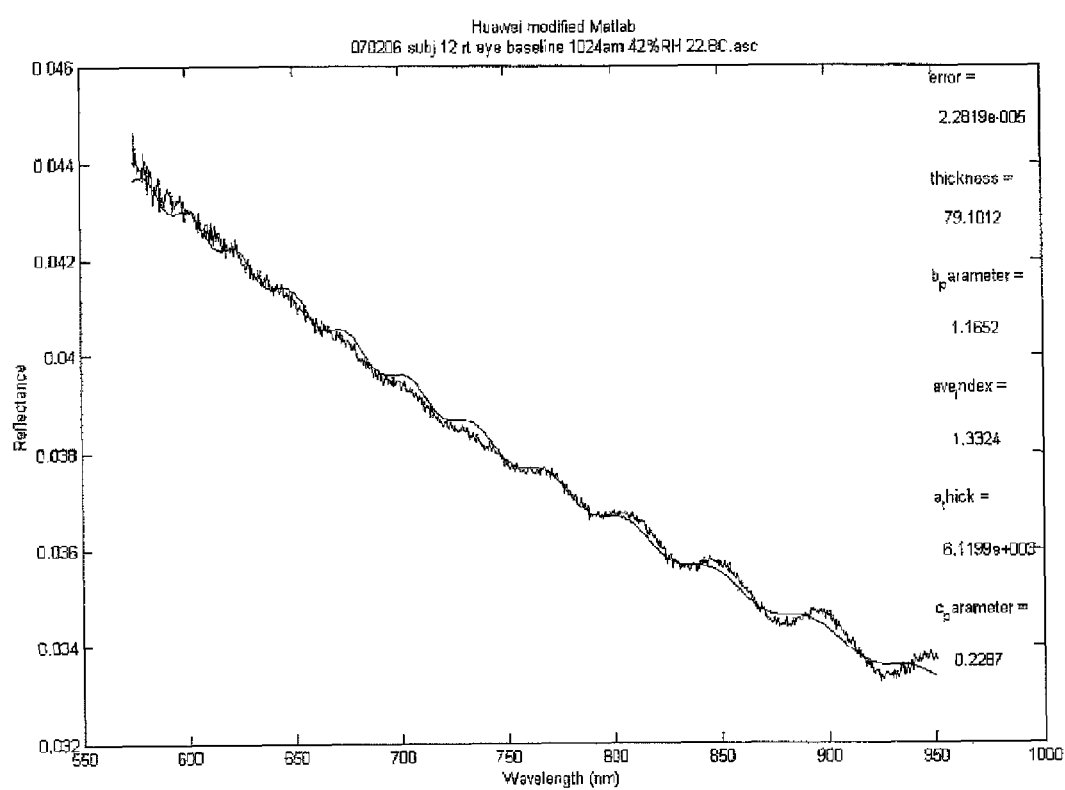
FIG. 6 shows the calculated tear film reflectance spectrum fit (smooth line) compared to the interferometer measured reflectance spectrum (line with noise) with the (exp($-cc*1000/\lambda$)) term in the equation for total reflectance.

An interferometric reflectance spectrum of a human subject's right eye baseline tear film is taken, as described in U.S. Pat. No. 7,963,655 B2. Measured reflectance data are processed according to the method of the present invention without and with the application of the correction with the (exp (−cc*1000/λ)) term in the equation for total reflectance, R. FIGS. 5 and 6 show the calculated tear film reflectance spectrum fits (smooth lines) compared to the interferometer measured reflectance spectra (lines with noise). FIG. 5 shows that application of the method of the invention without the (exp (−cc*1000/λ)) term in the equation for total reflectance, R, results in a poor fit of the calculated tear film reflectance spectrum (smooth line) to that of the measured reflectance spectrum (line with noise). The lipid layer thickness is calculated to be 34 nm in this case. FIG. 6 shows that application of the method of the invention with the (exp (−cc*1000/λ)) term in the equation for total reflectance, R, results in a good fit of the calculated tear film reflectance spectrum (smooth line) to that of the measured reflectance spectrum (line with noise). The lipid layer thickness is calculated to be 79 nm in this case. This lipid layer thickness value is considered to be within the range of values considered non-deficient. Aqueous layer thicknesses are similar in both cases, 6.040 and 6.120 microns respectively, for FIGS. 5 and 6. An aqueous layer thickness value well above a value of 3 microns is indicative of either benign reflex tearing or tearing due to the presence of a foreign body or inflammatory process. A determination between these alternatives was not made. Calculations for the refractive index of the corneal epithelium are different, 1.3346 and 1.3324 respectively, for FIGS. 5 and 6.

Example 4

Figure 7:
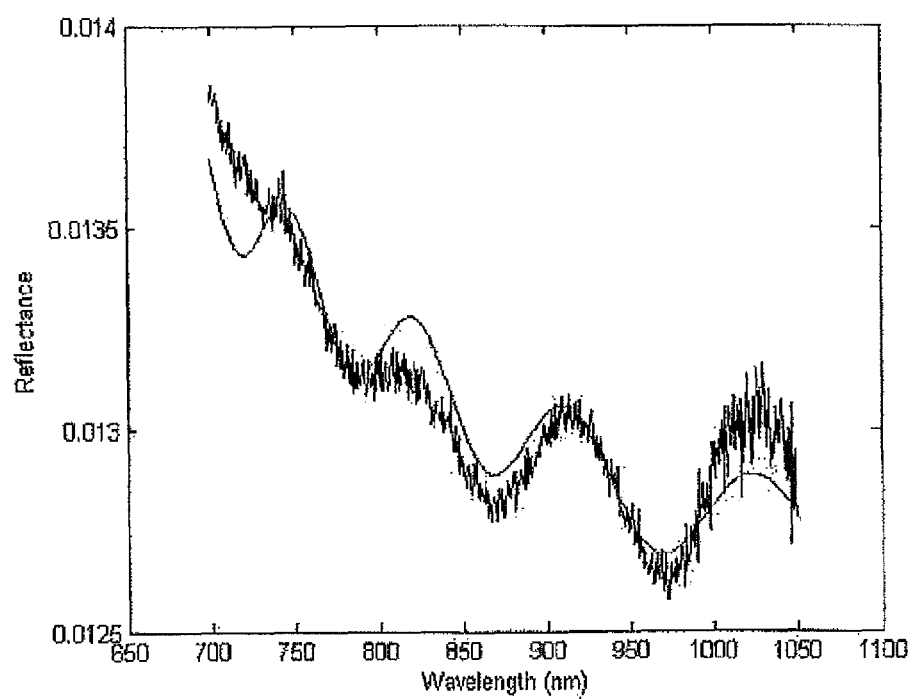
FIG. 7 shows the calculated tear film reflectance spectrum fit (smooth line) compared to the interferometer measured reflectance spectrum (line with noise) with the (exp($-cc*1000/\lambda$)) term in the equation for total reflectance.
Figure 8:
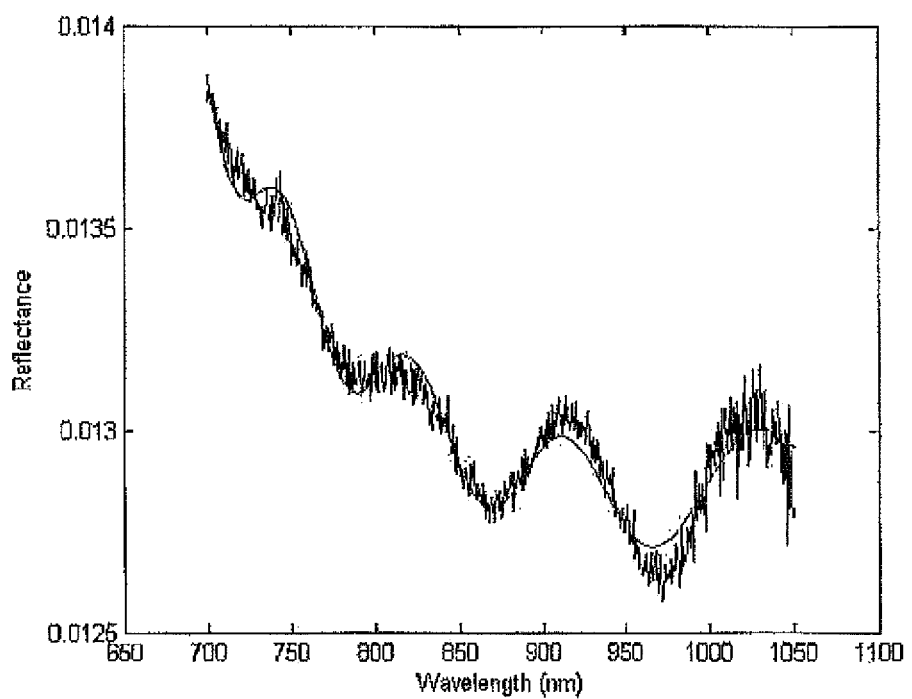
FIG. 8 shows the calculated tear film reflectance spectrum fit (smooth line) compared to the interferometer measured reflectance spectrum (line with noise) with the (exp($-a(1000/\lambda)+b(1000/\lambda)^2$) term in the equation for total reflectance.

An interferometric reflectance spectrum of a human subject's right eye baseline tear film is taken, as described in U.S. Pat. No. 7,963,655 B2. Measured reflectance data are processed according to the method of the present invention without and with the application of the correction with the term $(\exp(-a(1000/\lambda)+b(1000/\lambda)^2)$, wherein a and b are numbers, in the equation for total reflectance, R. FIGS. 7 and 8 show the calculated tear film reflectance spectrum fits (smooth lines) compared to the interferometer measured reflectance spectra (lines with noise). FIG. 7 shows that application of the method of the invention with the $(\exp(-cc*1000/\lambda)$ term in the equation for total reflectance, R, results in a poor fit of the calculated tear film reflectance spectrum (smooth line) to that of the measured reflectance spectrum (line with noise). The lipid layer thickness is calculated to be 37.8 nm in this case. FIG. 8 shows that application of the method of the invention with the $(\exp(-a(1000/\lambda)+b(1000/\lambda)^2)$ term in the equation for total reflectance, R, results in a good fit of the calculated tear film reflectance spectrum (smooth line) to that of the measured reflectance spectrum (line with noise). The lipid layer thickness is calculated to be 86.1 nm in this case. Aqueous layer thicknesses are similar in both cases, 3.040 and 2.985 microns respectively, for FIGS. 7 and 8. Again, these lipid and aqueous layer thickness values are considered to be within the range of values considered non-deficient. Calculations for the refractive index of the corneal epithelium are similar, 1.3344 and 1.3349 respectively, for FIGS. 7 and 8. The additional exponential term, $b(1000/\lambda)^2$, is believed to account for a Gaussian corneal surface roughness factor, occurring simultaneously with a non-Gaussian surface roughness, accounted for by the $(-a(1000/\lambda))$ term, within the relative large imaged surface area (12.5×133 microns).

Example 5

Interferometric reflectance spectra of human subject's right eye baseline tear films are taken, as described in U.S. Pat. No. 7,963,655 B2. Measured reflectance data are processed according to the method of the present invention with the application of the correction with either the $(\exp(-cc*1000/\lambda))$ or $(\exp(-a(1000/\lambda)+b(1000/\lambda)^2)$; subject 2, scans CJ through CN) term and consistently with the bb term in the equation for total reflectance, R. Table 1 presents results of simultaneous measurements and calculations of tear film lipid and aqueous layer thicknesses and corneal surface refractive index. Tear film lipid and aqueous layer thickness values are consistent with literature (King-Smith P E, Fink B A, Fogt N, Nichols K K, Hill R M, Wilson G S. The Thickness of the Human Precorneal Tear Film Evidence from reflection Spectra. *Invest Ophthalmol Vis Sci.* 2000; 41:3348-3359; Korb D R, Baron D F, Herman J P, Finnemore V M, Exford J M, Hermosa J L, Leahy C D, Glonek T, Greiner W. Tear film lipid layer thickness as a function of blinking. *Cornea.* 1994; 13(4): 354-359). Lipid thickness range=34-119 nm, mean=74 nm, stdev=23 nm and aqueous thickness range=1546-3870 nm, mean=2639 nm and stdev=403 nm. A tear lipid layer thickness of 34 nm potentially represents a tear lipid deficiency. An aqueous layer thickness of 1546 nm potentially represents a tear aqueous deficiency. Corneal surface refractive index range=1.3288-1.3386, mean=1.3328 and stdev=0.0024. Intrasubject refractive index stdev for 6 subjects, n≥5 measurements, were: 0.0010, 0.0009, 0.0006, 0.0009, 0.0010 and 0.0027.

TABLE 1

Clinical studies OPIN-101-Sys and 103

| subject# | scan# | lipid t, nm | Aqueous t, nm | Nd | Nd stdev |
|---|---|---|---|---|---|
| 1 | 29 | 34 | 3263 | 1.3346 | |
| 1 | 115 | 38 | 3256 | 1.3334 | |
| 1 | 116 | 38 | 3222 | 1.3333 | |
| 1 | 117 | 36 | 3128 | 1.3332 | |
| 1 | 118 | 29 | 2967 | 1.3319 | |
| 1 | 119 | 53 | 2909 | 1.3318 | |
| sub1 mean & stdev | | | | 1.3330 | 0.0010 |
| 2 | AY | 76 | 2548.9 | 1.3312 | |
| 2 | BY | 97 | 2629.1 | 1.3347 | |
| 2 | BZ | 101 | 2615.2 | 1.3346 | |
| 2 | CI | 89 | 2355 | 1.3308 | |
| 2 | CJ | 75.6 | 2368 | 1.3309 | |
| 2 | CK | 76.9 | 3143 | 1.3313 | |
| 2 | CL | 74.8 | 2846 | 1.3318 | |
| 2 | CM | 77.7 | 2750 | 1.3313 | |
| 2 | CN | 81.5 | 2669 | 1.331 | |
| 2 | CO | 87 | 2631 | 1.3312 | |
| 2 | CP | 93 | 2604 | 1.3312 | |
| 2 | CQ | 108 | 2582.1 | 1.3309 | |
| 2 | CR | 106 | 2566 | 1.3311 | |
| 2 | CS | 95 | 2561.5 | 1.3309 | |
| 2 | CT | 90 | 2554.1 | 1.3313 | |
| 2 | CU | 94 | 2541.6 | 1.3312 | |
| 2 | CV | 96 | 2525.8 | 1.3312 | |
| 2 | CW | 103 | 2513.5 | 1.331 | |
| 2 | CX | 101 | 2503.7 | 1.3311 | |
| 2 | CY | 105 | 2491.5 | 1.3312 | |
| 2 | CZ | 105 | 2478.5 | 1.3314 | |
| 2 | DA | 101 | 2469.6 | 1.3315 | |
| 2 | DB | 100 | 2484 | 1.3306 | |
| 2 | DC | 97 | 2481 | 1.3308 | |
| 2 | DD | 92 | 2480 | 1.3306 | |
| 2 | DE | 101 | 2468 | 1.3308 | |
| 2 | 54 | 88 | 2491 | 1.3317 | |
| 2 | 49 | 80 | 2550 | 1.331 | |
| 2 | 39 | 99 | 2795 | 1.3311 | |
| 2 | 50 | 75 | 2551 | 1.3309 | |
| sub2 mean & stdev | | | | 1.3313 | 0.0009 |
| 3 | 10 | 72 | 1867.2 | 1.3359 | |
| 3 | 15 | 71 | 1546.4 | 1.3368 | |
| 3 | 55 | 58 | 1628 | 1.3352 | |
| 3 | 56 | 66 | 1523 | 1.3358 | |
| 3 | 100 | 79 | 2068 | 1.3358 | |
| sub3 mean & stdev | | | | 1.3359 | 0.0006 |
| 4 | 5 | 37 | 1991 | 1.3382 | |
| 4 | 26 | 39 | 2181 | 1.3386 | |
| sub4 mean & stdev | | | | 1.3384 | 0.0003 |
| 5 | 121 | 102 | 2065 | 1.3341 | |
| 6 | 6 | 60 | 3905 | 1.3347 | |
| 6 | 7 | 71 | 3870.1 | 1.3351 | |
| 6 | 55 | 57 | 3412.5 | 1.3349 | |
| 6 | 84 | 94 | 3217.2 | 1.3369 | |
| 6 | 137 | 60 | 3171.6 | 1.3359 | |
| 6 | 137 | 96 | 3137 | 1.3365 | |
| sub6 mean & stdev | | | | 1.3357 | 0.0009 |
| 7 | 49 | 99 | 2470.4 | 1.3288 | |
| 7 | 26 | 36 | 2626 | 1.3306 | |
| 7 | 27 | 59 | 2594 | 1.3303 | |
| 7 | 47 | 108 | 2469.9 | 1.3288 | |
| 7 | 77 | 55 | 2477.9 | 1.3308 | |
| sub7 mean & stdev | | | | 1.3299 | 0.0010 |
| 8 | 25 | 105 | 3704 | 1.3306 | |
| 10 | 11 | 53 | 2465 | 1.3349 | |
| 10 | 12 | 50 | 2386 | 1.3339 | |
| 10 | 16 | 37 | 2431 | 1.3293 | |
| 10 | 17 | 63 | 2594 | 1.3354 | |
| 10 | 18 | 38 | 2462 | 1.3306 | |
| sub10 mean & stdev | | | | 1.3328 | 0.0027 |
| 12 | 93 | 85 | 4004.4 | 1.3349 | |
| 103S1 | 4 | 62 | 2563.4 | 1.3345 | |
| 103S2 | 5 | 59.8 | 2162.1 | 1.3307 | |
| 103S3 | 1 | 54 | 3610.8 | 1.3303 | |
| 103S4 | 2 | 76.6 | 2103.3 | 1.336 | |
| 103S6 | 3 | 50.7 | 2783.5 | 1.3341 | |
| 103S9 | 21 | 73.9 | 1807.4 | 1.3306 | |

TABLE 1-continued

Clinical studies OPIN-101-Sys and 103

| subject# | scan# | lipid t, nm | Aqueous t, nm | Nd | Nd stdev |
|---|---|---|---|---|---|
| 103S12 | 1 | 67.4 | 2330.1 | 1.3312 | |
| 103S8 | 1 | 65 | 3672.4 | 1.3376 | |
| 103S15 | 25 | 119.1 | 2074.7 | 1.3314 | |
| 103S16 | 25 | 36.98 | 2565.5 | 1.3337 | |
| 103S17 | 5 | 72 | 2697.3 | 1.3364 | |
| 103S18 | 10 | 36.8 | 3254.1 | 1.3335 | |
| 103S19 | 3 | 45.33 | 1988.2 | 1.3366 | |
| 103S20 | 3 | 86.3 | 3301.4 | 1.3354 | |
| 103S21 | 5 | 58.6 | 1998.7 | 1.3354 | |
| | | | mean | 1.3328 | 0.0024 |

Figure 9:
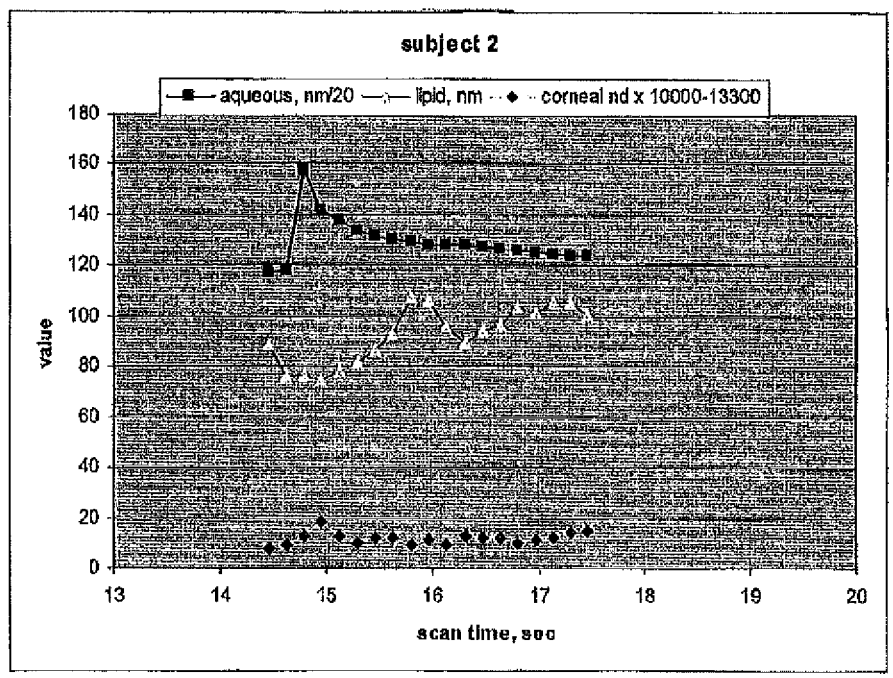
FIG. 9 shows temporal changes in tear film and corneal surface parameters in Subject 2.

Table 2 and FIG. 9 show the time sequence of tear film lipid, aqueous and conical surface refractive index measurements, taken from a subset of subject 2 data in Table 1. The type of exponential term (exp term) used to correct for surface roughness for each spectrum in Table 2 is referenced by way of referring to the preceding example in which it was used, e.g. Ex. 1 or Ex. 2. Sequential interferometric measurements were taken for subject 2 every 0.168 msec for a 25.2 second period. Data in Table 2 present scan data from 14.448-17.472 seconds. Tear film aqueous layer thickness in nanometers (nm) was divided by 20 for plotting purpose. Corneal surface refractive index was multiplied by 10000 and then 13300 was subtracted from this for plotting purposes. This time interval was selected because it encompasses a single eyelid blink at 14.784 seconds, visualized by a sudden increase in tear film aqueous layer thickness from 2368 nm to 3143 nm. It is also seen that the tear film lipid layer thickness rose from a minimum thickness of 75.6 nm at 14.616 seconds just before the blink, to a maximum of 107.6 nm at 15.792 seconds after the blink. Thus, the tear film lipid layer increased in thickness by 32.0 nm in 1.176 seconds. This change in thickness following a blink is consistent with the average change in tear film lipid layer thickness reported by Korb (Korb D R, Baron D F, Heiman J P, Finnemore V M, Exford J M, Hermosa J L, Leahy C D, Glonek T, Greiner J V. Tear film lipid layer thickness as a function of blinking. *Cornea.* 1994; 13(4): 354-359) of 33 nm following a blink among individuals with baseline tear film lipid layer thicknesses of 75-150 nm. It is seen that the corneal surface refractive index does not change much following the blink in this subject. These temporal changes in tear film and corneal surface parameters require further study and it is seen that the methods of the present invention will be useful in that regard.

TABLE 2

Subject 2 scan time data from Table 1.

| scan | time, sec | lipid nm | aq nm | nd | (nd × 10000) − 13300 aq/20 | exp term |
|---|---|---|---|---|---|---|
| CI | 14.448 | 88.7 | 2355 | 1.3308 | 117.75 | 8 | Ex. 1 |
| CJ | 14.616 | 75.6 | 2368 | 1.3309 | 118.4 | 9 | Ex. 4 |
| CK | 14.784 | 76.9 | 3143 | 1.3313 | 157.15 | 13 | Ex. 4 |
| CL | 14.952 | 74.8 | 2846 | 1.3318 | 142.3 | 18 | Ex. 4 |
| CM | 15.12 | 77.7 | 2750 | 1.3313 | 137.5 | 13 | Ex. 4 |
| CN | 15.288 | 81.5 | 2669 | 1.331 | 133.45 | 10 | Ex. 4 |
| CO | 15.456 | 86.8 | 2631 | 1.3312 | 131.55 | 12 | Ex. 1 |
| CP | 15.624 | 92.5 | 2604 | 1.3312 | 130.2 | 12 | Ex. 1 |
| CQ | 15.792 | 107.6 | 2582.1 | 1.3309 | 129.105 | 9 | Ex. 1 |
| CR | 15.96 | 106.0 | 2566 | 1.3311 | 128.3 | 11 | Ex. 1 |
| CS | 16.128 | 95.4 | 2561.5 | 1.3309 | 128.075 | 9 | Ex. 1 |
| CT | 16.296 | 89.6 | 2554.1 | 1.3313 | 127.705 | 13 | Ex. 1 |
| CU | 16.464 | 94.1 | 2541.6 | 1.3312 | 127.08 | 12 | Ex. 1 |
| CV | 16.632 | 96.1 | 2525.8 | 1.3312 | 126.29 | 12 | Ex. 1 |
| CW | 16.8 | 103.2 | 2513.5 | 1.331 | 125.675 | 10 | Ex. 1 |
| CX | 16.968 | 101.4 | 2503.7 | 1.3311 | 125.185 | 11 | Ex. 1 |
| CY | 17.136 | 105.4 | 2491.5 | 1.3312 | 124.575 | 12 | Ex. 1 |
| CZ | 17.304 | 105.4 | 2478.5 | 1.3314 | 123.925 | 14 | Ex. 1 |
| DA | 17.472 | 100.5 | 2469.6 | 1.3315 | 123.48 | 15 | Ex. 1 |

Figure 10:
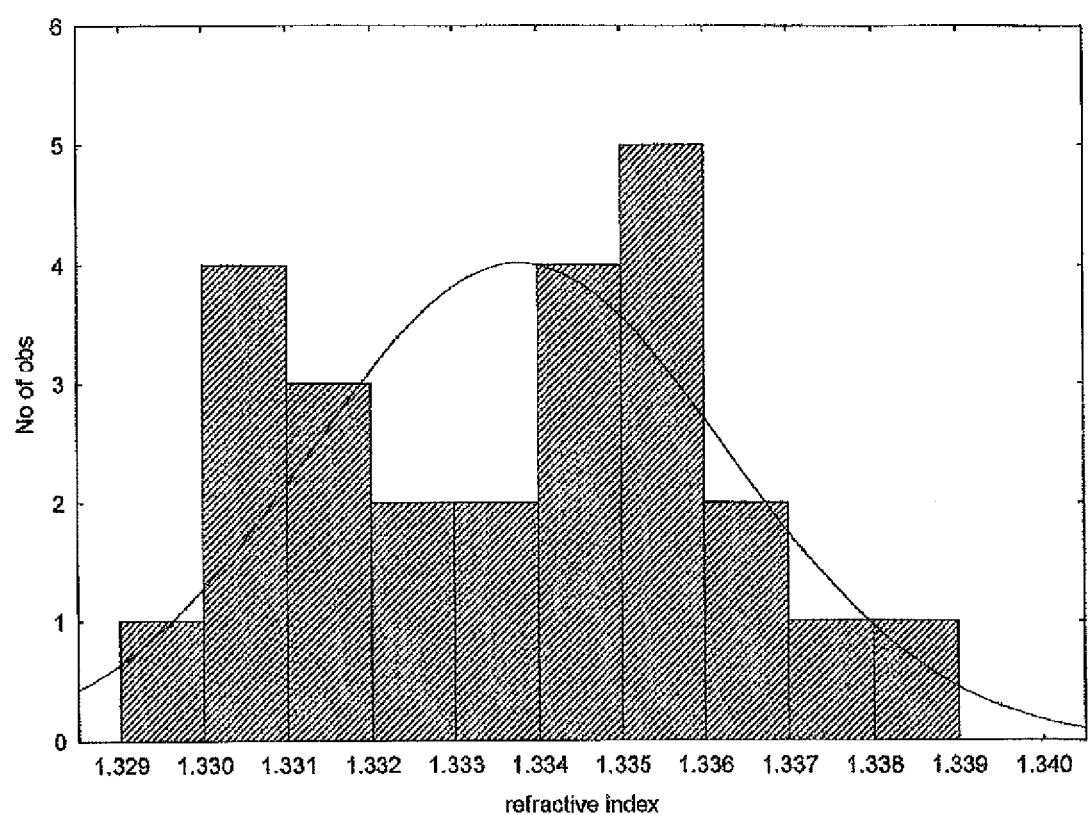
FIG. 10 shows a histogram of corneal surface refractive index (n=25). Deviation from normal distribution (smooth curve) shown. Values range from above pure water at 35° C. (1.32737) through and above the range of values reported for human tear film ($n_d$=1.3346–1.3371).

Table 3 presents average corneal surface refractive index calculations taken from data in Table 1, along with refractive index data from subjects wherein a single measurement was taken. FIG. 10 shows a histogram plot of the data in Table 3. It is seen that corneal surface refractive index values range from above that of pure water at the ocular surface temperature of 35° C. (132737) through and above the range of values reported for the human tear film ($n_d$=1.3346-1.3371; Golding T R, Brennan N A. Tear refractive index in dry and normal eyes. *Clin Exper Optom Suppl* 1991; 74(6):212). Refractive index distribution was bimodal, with peaks at 1.3300-1.3310 and 1.3350-1.3360, wherein 15 out of 25 subjects had mean values lower than a low reported value of 1.3346 for the tear film. Corneal surface refractive index values comparable to those of the tear film confirm a prior hypothesis (King-Smith P E, Fink B A, Fogt N, Nichols K K, Hill R M, Wilson G S. The Thickness of the Human Precorneal Tear Film: Evidence from reflection Spectra. *Invest Ophthalmol Vis Sci.* 2000; 41:3348-3359). Corneal surface refractive index values lower than those of the aqueous tear were unexpected. Nonetheless, lower values are consistent with the hypothesis that transmembrane mucin chains extending into the aqueous tear film expel some non-cationic tear proteins between the chains at the interface, since tear proteins otherwise contribute to tear refractive index (Golding T R, Brennan N A. Tear refractive index in dry and normal eyes. *Clin Exper Optom Suppl.* 1991; 74(6):212). This proposed mechanism of tear protein expulsion is similar to the mechanism wherein polyethylene glycol-modified surfaces expel proteins.

TABLE 3

| subject# | nd (ave for n > 1) | no. of obs., n |
|---|---|---|
| OP101S1ave | 1.3330 | 6 |
| OP101S2ave | 1.3313 | 30 |
| OP101S3ave | 1.3359 | 5 |
| OP101S4ave | 1.3384 | 2 |
| OP101S5scan121 | 1.3341 | 1 |
| OP101S6ave | 1.3357 | 6 |
| OP101S7ave | 1.3299 | 5 |
| OP101S8scan25 | 1.3306 | 1 |
| OP101S10ave | 1.3328 | 5 |
| OP101S12scan93 | 1.3349 | 1 |
| 103S1scan4 | 1.3345 | 1 |
| 103S2scan5 | 1.3307 | 1 |
| 103S3scan1 | 1.3303 | 1 |
| 103S4scan2 | 1.336 | 1 |
| 103S6scan3 | 1.3341 | 1 |
| 103S9scan21 | 1.3306 | 1 |
| 103S12scan1 | 1.3312 | 1 |
| 103S8scan1 | 1.3376 | 1 |
| 103S15scan25 | 1.3314 | 1 |
| 103S16scan25 | 1.3337 | 1 |
| 103S17scan5 | 1.3364 | 1 |
| 103S18scan10 | 1.3335 | 1 |

TABLE 3-continued

| subject# | nd (ave for n > 1) | no. of obs., n |
|---|---|---|
| 103S19scan3 | 1.3366 | 1 |
| 103S20scan3 | 1.3354 | 1 |
| 103S21scan5 | 1.3354 | 1 |

Example 6

Figure 11:
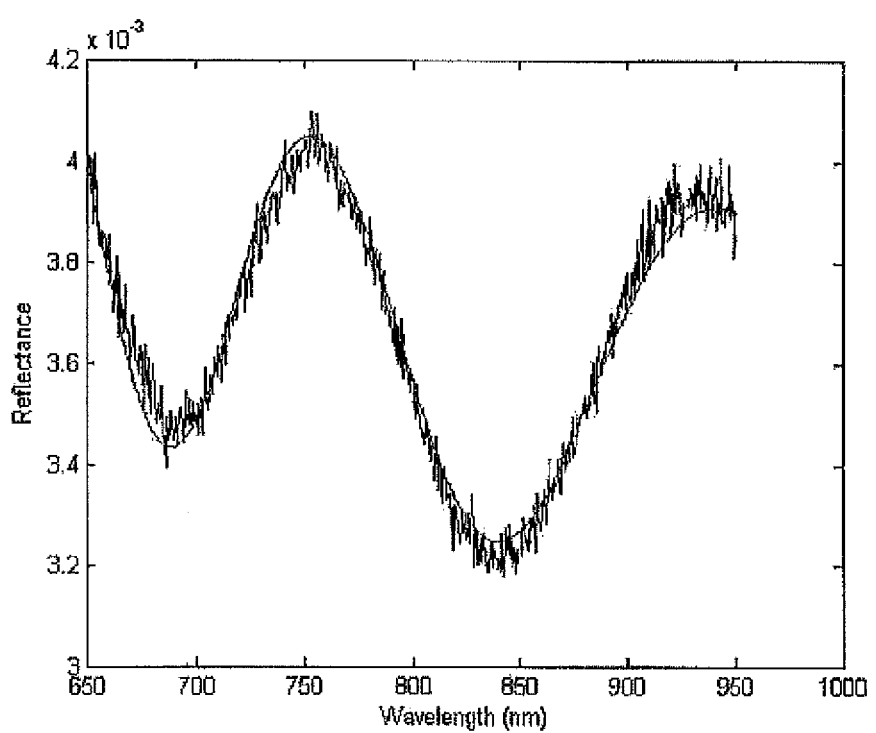
FIG. 11 shows the calculated tear film reflectance spectrum fit (smooth line) compared to the interferometer measured reflectance spectrum (line with noise).

An interferometric reflectance spectrum of a human subject's (rh33) baseline tear film is taken, as described in U.S. Pat. No. 7,963,655 B2, while the subject was wearing an ACUVUE® 2 soft hydrogel contact lens. Measured reflectance data are processed according to the method of the present invention with the application of the correction with the (exp (−cc*1000/λ)) and bb terms in the equation for total reflectance, R. The application of the method of the invention to contact lens wearers requires the use of the contact lens refractive index as a starting value for refractive index, instead of the refractive index starting value of $1.338+0.00306*(1000/\lambda)^2$ used for non-contact lens wearers. In this case, a value of $1.4053+0.00306*(1000/\lambda)^2$ was used, as this is the published value for refractive index of the ACUVUE® 2 soft hydrogel contact lens (1.4053), along with an assumed dispersion factor of $0.00306*(1000/\lambda)^2$. FIG. 11 shows the calculated tear film reflectance spectrum (smooth line) compared to the interferometer measured reflectance spectrum (line with noise). An excellent fit is obtained. A tear film lipid layer thickness of 38.6 nm was calculated, along with a tear film aqueous layer thickness of 1365.4 nm and a contact lens surface refractive index of 1.3553. These tear film lipid and aqueous layer thickness values are substantially lower than those of an individual without tear lipid or aqueous layer deficiencies who is not wearing a contact lens and are generally consistent with the known thinner tear film lipid and aqueous layers among contact lens wearers. While the 1.3553 refractive index is considerably lower than that of a reported value of 1.4053 for the ACUVUE® 2 lens, the refractive index of this lens has also been reported to be a low as 1.361 (M. Lira et al. *Contact Lens & Anterior Eye* 31 (2008) 89-94). Moreover, without wishing to be bound by any particular theory, it is known that ACUVUE® 2 soft hydrophilic hydrogel contact lens surfaces have considerable water-binding capacity, which could lower the surface refractive index from that of the bulk polymer. Also, it is known that these and other contact lenses adsorb proteins such as tear mucins, with considerable water-binding capacity, which may also result in a lower contact lens surface refractive index. It is anticipated that in-vivo contact lens surface refractive index measurements will be related to surface hydrophilicity and macroscopic contact lens surface wetting in-eye, an important parameter relating to contact lens comfort.

What is claimed is:

1. A method of evaluating an ocular environment of a patient comprising:
    (a) selecting the patient;
    (b) aligning an eye of the patient with light originating from a light source;
    (c) measuring light reflectance from the eye;
    (d) fitting the light reflectance to a mathematical construct based upon a characteristic mathematical matrix of a thin film stack comprising in sequence from top to bottom: air as a boundary, a tear film lipid layer, a tear film aqueous layer and a contact lens as a semi-infinite substrate; and
    (e) determining a parameter selected from the group consisting of lipid layer thickness, aqueous layer thickness and contact lens surface refractive index.

2. The method of claim 1, wherein the light reflectance is from the tear film, the contact lens surface or a combination thereof.

3. The method of claim 1, wherein the determined parameter is compared to a reference value.

4. The method as in claim 1, wherein the measuring is performed using an interferometer.

5. The method as in claim 1, wherein the method includes adjusting the mathematical construct based on a factor selected from the group consisting of (a) an adjustment for tear film and contact lens surface light reflectance and (b) an adjustment for substrate roughness.

6. The method as in claim 5, wherein the adjustment for tear film and contact lens surface light reflectance is a number.

7. The method as in claim 5, wherein the adjustment for substrate roughness is selected from mathematical terms comprising $\exp(-cc*1000/\lambda)$ and $\exp(-a*1000/\lambda)+b*1000/\lambda)^2$, wherein cc, a and b are numbers.

8. The method as in claim 5, wherein the adjustment for substrate roughness is selected from mathematical terms comprising a non-Gaussian height distribution function or term.

9. A method of evaluating an ocular environment of a patient comprising the steps of:
    (a) selecting the patient;
    (b) aligning an eye of the patient with light originating from a light source;
    (c) measuring light reflectance of the eye;
    (d) fitting the light reflectance to a mathematical construct based upon a characteristic mathematical matrix of a thin film stack comprising in sequence from top to bottom: air as a boundary, a tear film lipid layer, a tear film aqueous layer and a contact lens as a semi-infinite substrate;
    (e) determining a first parameter selected from the group consisting of lipid layer thickness, aqueous layer thickness and contact lens surface refractive index; and
    (f) comparing the first parameter with known parameters for patients with known tear film or contact lens surface characteristics.

10. The method as in claim 9, wherein the measurement of light reflectance is performed using an interferometer.

11. The method as in claim 9, wherein the method includes adjusting the mathematical construct based on a factor selected from the group consisting of (a) an adjustment for tear film and contact lens surface light reflectance and (b) an adjustment for substrate roughness.

12. The method as in claim 11, wherein the adjustment for tear film and contact lens surface light reflectance is a number.

13. The method as in claim 11, wherein the adjustment for substrate roughness is selected from mathematical terms comprising $\exp(-cc*1000/\lambda)$ and $\exp(-a*1000/\lambda)+b*1000/\lambda)^2$, wherein cc, a and b are numbers.

14. The method as in claim 11, wherein the adjustment for substrate roughness is selected from mathematical terms comprising a non-Gaussian height distribution function or term.

15. A method of evaluating an ocular environment of a patient comprising the steps of:
    (a) selecting the patient;
    (b) aligning an eye of the patient with light originating from a light source;
    (c) measuring light reflectance from the eye;

(d) fitting the light reflectance to a mathematical construct based upon a characteristic mathematical matrix of a thin film stack comprising in sequence from top to bottom: air as a boundary, a tear film lipid layer, a tear film aqueous layer and a contact lens as a semi-infinite substrate; and (e) calculating at least one of (a) tear film lipid layer thickness, (b) tear film aqueous layer thicknesses, and (c) refractive index of the contact lens surface of the patient using the mathematical construct.

16. The method as in claim 15, wherein the measurement of light reflectance is performed using an interferometer.

17. The method as in claim 15, wherein the method includes adjusting the mathematical construct based on a factor selected from the group consisting of (a) an adjustment for tear film and contact lens surface light reflectance and (b) an adjustment for substrate roughness.

18. The method as in claim 17, wherein the adjustment for tear film and contact lens surface light reflectance is a number.

19. The method as in claim 17, wherein the adjustment for substrate roughness is selected from mathematical terms comprising $\exp(-cc*1000/\lambda)$ and $\exp(-a*1000/\lambda)+b*1000/\lambda^{\wedge}2)$, wherein cc, a and b are numbers.

20. The method as in claim 17, wherein the adjustment for substrate roughness is selected from mathematical terms comprising a non-Gaussian height distribution function or term.

\* \* \* \* \*